US008497067B2

(12) United States Patent
Loudig

(10) Patent No.: US 8,497,067 B2
(45) Date of Patent: Jul. 30, 2013

(54) RESTORATION OF NUCLEIC ACID FROM DEGRADED OR FORMALIN-FIXED AND PARAFFIN-EMBEDDED TISSUE AND USES THEREOF

(75) Inventor: Olivier Loudig, Fleetwood, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 1137 days.

(21) Appl. No.: 12/087,951

(22) PCT Filed: Feb. 26, 2007

(86) PCT No.: PCT/US2007/004892
§ 371 (c)(1),
(2), (4) Date: Mar. 17, 2009

(87) PCT Pub. No.: WO2007/103018
PCT Pub. Date: Sep. 13, 2007

(65) Prior Publication Data
US 2012/0009570 A1 Jan. 12, 2012

Related U.S. Application Data
(60) Provisional application No. 60/778,221, filed on Mar. 1, 2006.

(51) Int. Cl.
*C12P 19/34* (2006.01)
(52) U.S. Cl.
USPC ...................................... 435/6.11; 536/24.33
(58) Field of Classification Search
None
See application file for complete search history.

(56) References Cited

U.S. PATENT DOCUMENTS

2005/0196782 A1* 9/2005 Kiefer et al. ................ 435/6
2005/0239068 A1* 10/2005 Bosnes ....................... 435/6

OTHER PUBLICATIONS

Goff et al. (BMC Genomics, 2004, 5:76).*
Phillips et al. (Methods, 1996, 10(3), p. 283-288, IDS reference).*
Ishikawa et al. (Clinical Chemistry, 1997, 43:5, p. 764-770).*
Xiang et al. (Nucleic Acid Research, 2003, 31(9):e53, p. 1-5).*
Kitabayashi et al. (Biosci Biotech. Biochem., 2003, 67(11):2474-2476).*
Meyers et al. (Biochemistry, 1991, 30(31):7661-7666).*
Loudig et al. (Nucleic Acids Research, 2007, 35(15):e94, p. 1-14).*
International Preliminary Report on Patentability (9 pages) for related application PCT/US2007/004892 with an international filed of Feb. 26, 2007.
Phillips and Eberwine, entitled "Antisense RNA Amplification: A Linear Amplification Method for Analyzing the mRNA Population from Single Living Cells," Methods: A Companion to Methods in Enzymology, 1996, vol. 10, pp. 283-288.

(Continued)

*Primary Examiner* — Stephanie K Mummert
(74) *Attorney, Agent, or Firm* — Amster, Rothstein & Ebenstein LLP

(57) ABSTRACT

This invention provides methods, primers and kits for restoration of nucleic acid from tissue, in particular degraded tissue and formalin-fixed and paraffin-embedded (FFPE) tissue, where the methods involve complementary-template reverse-transcription (CT-RT) where short single-stranded DNA sequences reverse-transcribed from mRNA are used for reverse-transcription of complementary sense-RNA templates. The methods can be used to determine patterns of gene expression and chromosomal alterations in archived tissue samples, and may be used to identify expression of disease-related genes.

18 Claims, 10 Drawing Sheets

OTHER PUBLICATIONS

Schlingemann J. et al., entitled "Effective transcriptome amplification for expression profiling on sense-oriented oligonucleotide microarrays," Nucleic Acids Research, 2005, vol. 33, No. 3, e29, pp. 1-12.

Notification of Transmittal of the International Serach Report and Written Opinion of the International Seraching Authority, or the Declaration (1 page) for related application PCT/US2007/004892 with an international filed of Feb. 26, 2007.

International Search Report (5 pages) for related application PCT/US2007/004892 with an international filed of Feb. 26, 2007.

Written Opinion (8 pages) for related application PCT/US2007/004892 with an international filed of Feb. 26, 2007.

Alexandersson et al., entitled "Whole gene family expression and drought stress regulation of aquaporins," Plant Molecular Biology, 2005, vol. 59, pp. 469-484.

Protoscript First Strand cDNA Synthesis Kit Instruction Manual, New Engladnd BioLabs, Inc., 2005, Version 1.4.

Invitation to Pay Additional Fees and, Where Applicable, Protest Fee (2 pages) for related application PCT/US2007/004892 with an international filed of Feb. 26, 2007.

\* cited by examiner

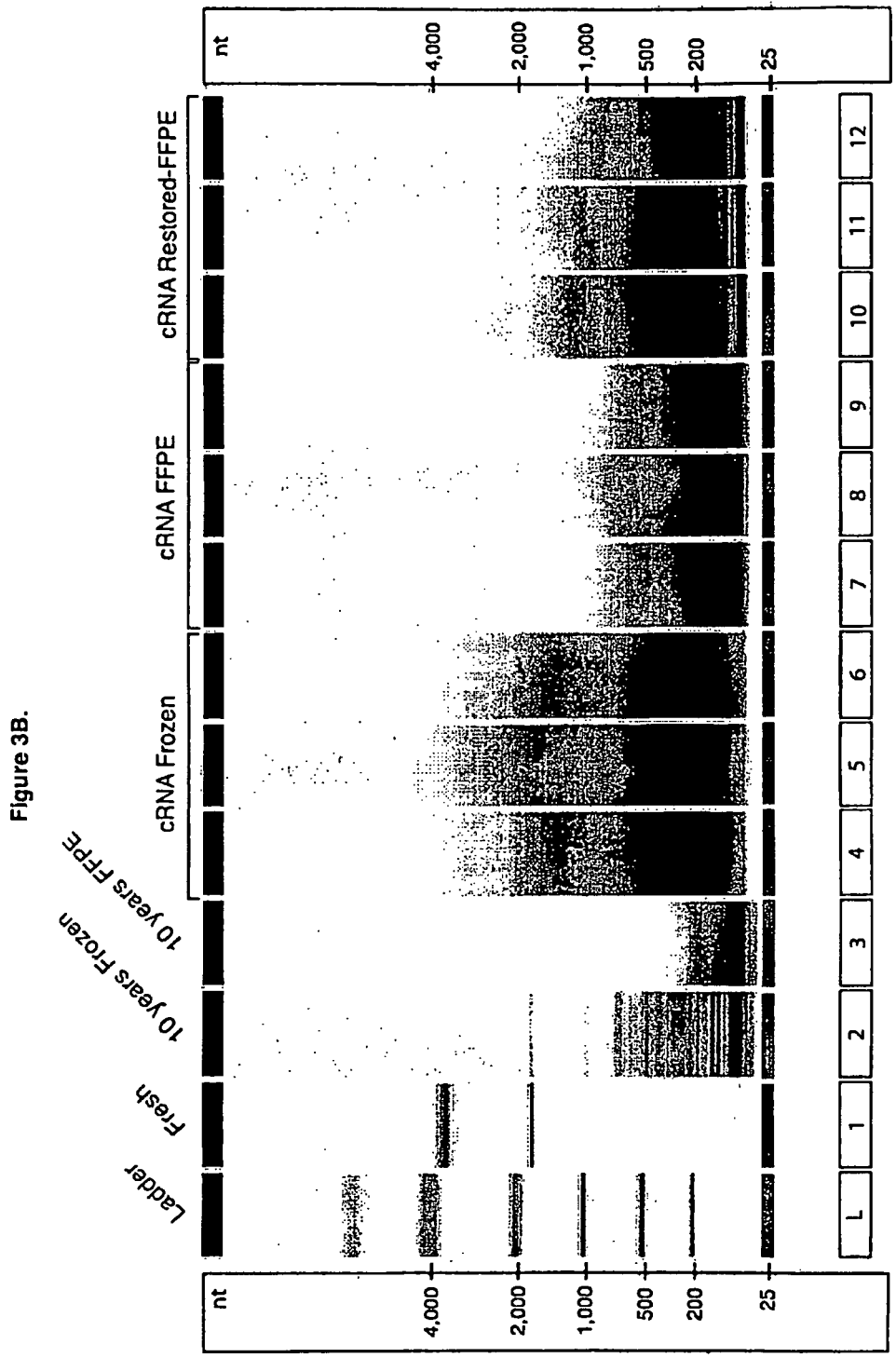

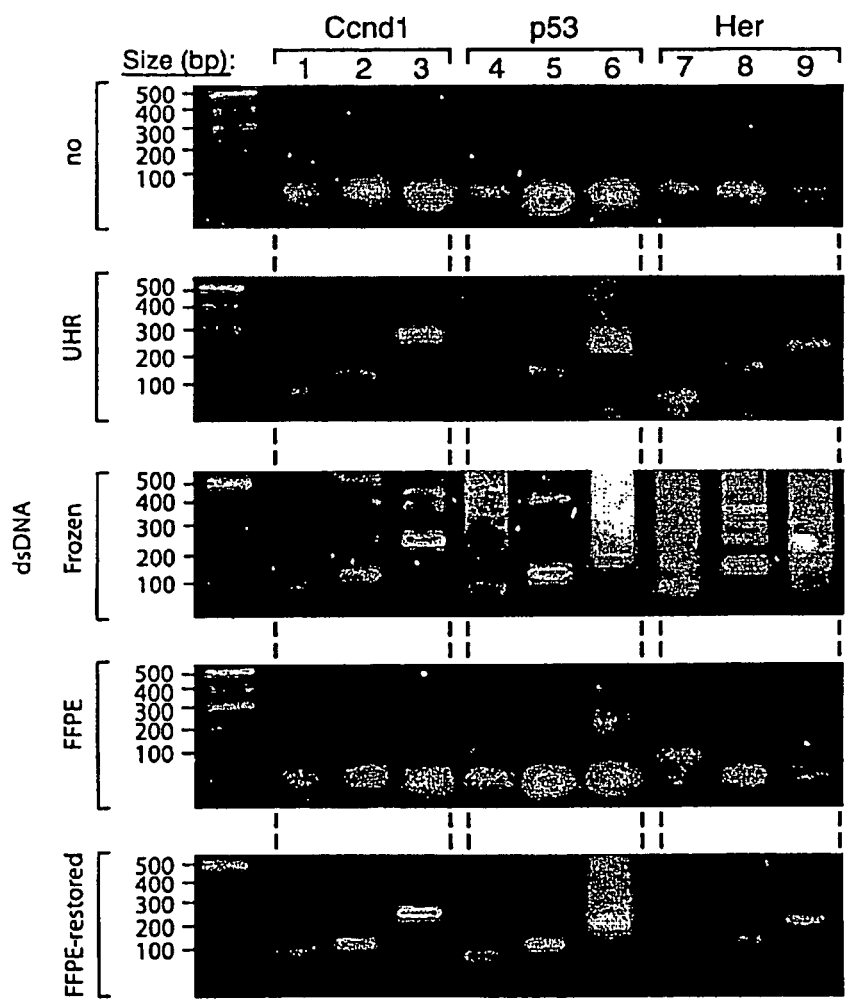

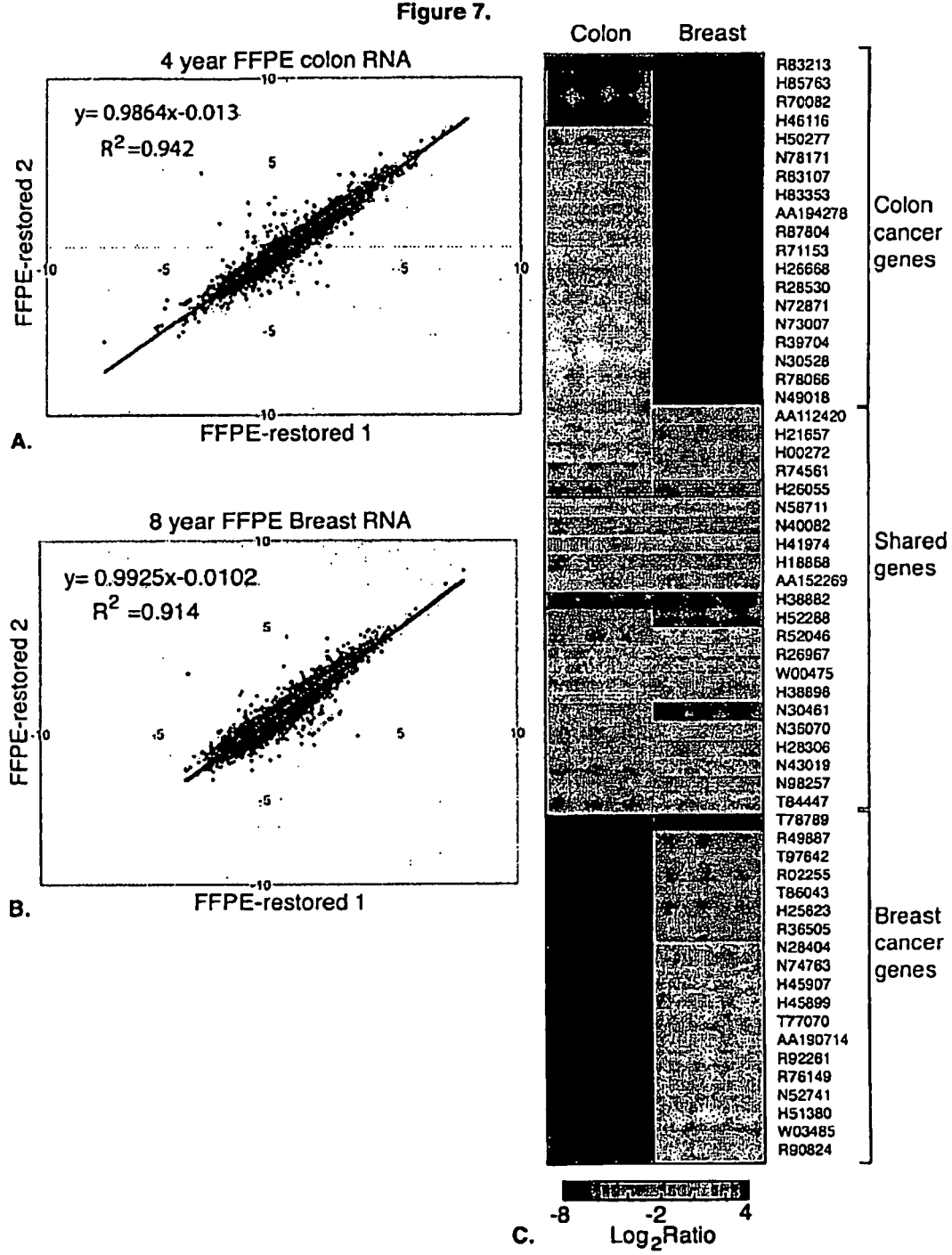

```
                              SEQUENCE LISTING

<160> NUMBER OF SEQ ID NOS: 24

<210> SEQ ID NO 1
<211> LENGTH: 23
<212> TYPE: DNA
<213> ORGANISM: Artificial Sequence
<220> FEATURE:
<223> OTHER INFORMATION: Primer directed to human gene

<400> SEQUENCE: 1
gtgatggggc aagggcacaa gtc                                              23

<210> SEQ ID NO 2
<211> LENGTH: 23
<212> TYPE: DNA
<213> ORGANISM: Artificial Sequence
<220> FEATURE:
<223> OTHER INFORMATION: Primer directed to human gene

<400> SEQUENCE: 2
cggctgggtc tgtgcatttc tgg                                              23

<210> SEQ ID NO 3
<211> LENGTH: 23
<212> TYPE: DNA
<213> ORGANISM: Artificial Sequence
<220> FEATURE:
<223> OTHER INFORMATION: Primer directed to human gene

<400> SEQUENCE: 3
cccagcacca acatgtaacc ggc                                              23

<210> SEQ ID NO 4
<211> LENGTH: 23
<212> TYPE: DNA
<213> ORGANISM: Artificial Sequence
<220> FEATURE:
<223> OTHER INFORMATION: Primer directed to human gene

<400> SEQUENCE: 4
tggggtttta ccagttttat ttc                                              23

<210> SEQ ID NO 5
<211> LENGTH: 23
<212> TYPE: DNA
<213> ORGANISM: Artificial Sequence
<220> FEATURE:
<223> OTHER INFORMATION: Primer directed to human gene

<400> SEQUENCE: 5
gctggtctca aactcctggg ctc                                              23
```

<210> SEQ ID NO 6
<211> LENGTH: 23
<212> TYPE: DNA
<213> ORGANISM: Artificial Sequence
<220> FEATURE:
<223> OTHER INFORMATION: Primer directed to human gene

<400> SEQUENCE: 6
gtggagctgg aagggtcaac atc                                              23

<210> SEQ ID NO 7
<211> LENGTH: 23
<212> TYPE: DNA
<213> ORGANISM: Artificial Sequence
<220> FEATURE:
<223> OTHER INFORMATION: Primer directed to human gene

<400> SEQUENCE: 7
cccacccttc ccctccttct ccc                                              23

<210> SEQ ID NO 8
<211> LENGTH: 26
<212> TYPE: DNA
<213> ORGANISM: Artificial Sequence
<220> FEATURE:
<223> OTHER INFORMATION: Primer directed to human gene

<400> SEQUENCE: 8
gcagcaaagt tttattgtaa aataag                                           26

<210> SEQ ID NO 9
<211> LENGTH: 23
<212> TYPE: DNA
<213> ORGANISM: Artificial Sequence
<220> FEATURE:
<223> OTHER INFORMATION: Primer directed to human gene

<400> SEQUENCE: 9
gcgacccatt cagagactgt ccc                                              23

<210> SEQ ID NO 10
<211> LENGTH: 23
<212> TYPE: DNA
<213> ORGANISM: Artificial Sequence
<220> FEATURE:
<223> OTHER INFORMATION: Primer directed to human gene

<400> SEQUENCE: 10
gtgtcagtat ccaggctttg tac                                              23

<210> SEQ ID NO 11
<211> LENGTH: 23
<212> TYPE: DNA
<213> ORGANISM: Artificial Sequence
<220> FEATURE:
<223> OTHER INFORMATION: Primer directed to human gene

<400> SEQUENCE: 11
ggggagaatg ggtgttgtat ggg                                              23

<210> SEQ ID NO 12
<211> LENGTH: 26
<212> TYPE: DNA
<213> ORGANISM: Artificial Sequence
<220> FEATURE:
<223> OTHER INFORMATION: Primer directed to human gene

```
<400> SEQUENCE: 12
tgcaaatgga caaagtgggt gtggag                                          26

<210> SEQ ID NO 13
<211> LENGTH: 39
<212> TYPE: DNA
<213> ORGANISM: Artificial Sequence
<220> FEATURE:
<223> OTHER INFORMATION: Promoter for human gene

<400> SEQUENCE: 13
ggccagtgaa ttgtattacg acacactata gggaggcgg                            39

<210> SEQ ID NO 14
<211> LENGTH: 39
<212> TYPE: DNA
<213> ORGANISM: Artificial Sequence
<220> FEATURE:
<223> OTHER INFORMATION: Complementary Promoter for human gene

<400> SEQUENCE: 14
ccgcctccct atagtgtgtc gtaatacaat tcactggcc                            39

<210> SEQ ID NO 15
<211> LENGTH: 29
<212> TYPE: DNA
<213> ORGANISM: Artificial Sequence
<220> FEATURE:
<223> OTHER INFORMATION: Promoter for human gene

<400> SEQUENCE: 15
gcgcgaaatt aaccctcact aaagggaga                                       29

<210> SEQ ID NO 16
<211> LENGTH: 29
<212> TYPE: DNA
<213> ORGANISM: Artificial Sequence
<220> FEATURE:
<223> OTHER INFORMATION: Complementary Promoter for human gene

<400> SEQUENCE: 16
tctcccttta gtgagggtta atttcgcgc                                       29

<210> SEQ ID NO 17
<211> LENGTH: 71
<212> TYPE: DNA
<213> ORGANISM: Artificial Sequence
<220> FEATURE:
<223> OTHER INFORMATION: Artificial primer
<220> FEATURE:
<221> NAME/KEY: misc_feature
<222> LOCATION: (40)..(69)
<223> OTHER INFORMATION: t is deoxyribothymidine; some t may be absent
      so that the number of "t" varies between 10-30
<220> FEATURE:
<221> NAME/KEY: misc_feature
<222> LOCATION: (71)..(71)
<223> OTHER INFORMATION: n is a, c, g or t

<400> SEQUENCE: 17
ggccagtgaa ttgtattacg acacactata gggaggcggt tttttttttt tttttttttt     60 ttttttttv n                                                           71

<210> SEQ ID NO 18
<211> LENGTH: 61
<212> TYPE: DNA
```

```
<213> ORGANISM: Artificial Sequence
<220> FEATURE:
<223> OTHER INFORMATION: Artificial primer
<220> FEATURE:
<221> NAME/KEY: misc_feature
<222> LOCATION: (30)..(59)
<223> OTHER INFORMATION: t is deoxyribothymidine; some "t" may be absent
      so that the number of "t" varies between 10-30
<220> FEATURE:
<221> NAME/KEY: misc_feature
<222> LOCATION: (61)..(61)
<223> OTHER INFORMATION: n is a, c, g or t

<400> SEQUENCE: 18
gcgcgaaatt aaccctcact aaagggagat ttttttttt tttttttttt tttttttttv      60 n                                                                    61

<210> SEQ ID NO 19
<211> LENGTH: 71
<212> TYPE: DNA
<213> ORGANISM: Artificial Sequence
<220> FEATURE:
<223> OTHER INFORMATION: Artificial primer
<220> FEATURE:
<221> NAME/KEY: misc_feature
<222> LOCATION: (1)..(1)
<223> OTHER INFORMATION: n is a, c, g or t
<220> FEATURE:
<221> NAME/KEY: misc_feature
<222> LOCATION: (3)..(32)
<223> OTHER INFORMATION: a is deoxyriboadenosine; some "a" may be absent
      so that the number of "a" varies between 10-30

<400> SEQUENCE: 19
nbaaaaaaaa aaaaaaaaaa aaaaaaaaaa aaccgcctcc ctatagtgtg tcgtaataca     60
attcactggc c                                                         71

<210> SEQ ID NO 20
<211> LENGTH: 61
<212> TYPE: DNA
<213> ORGANISM: Artificial Sequence
<220> FEATURE:
<223> OTHER INFORMATION: Primer directed to human gene
<220> FEATURE:
<221> NAME/KEY: misc_feature
<222> LOCATION: (1)..(1)
<223> OTHER INFORMATION: n is a, c, g or t
<220> FEATURE:
<221> NAME/KEY: misc_feature
<222> LOCATION: (3)..(32)
<223> OTHER INFORMATION: a is deoxyriboadenosine; some "a" may be absent
      so that the number of "a" varies between 10-30

<400> SEQUENCE: 20
nbaaaaaaaa aaaaaaaaaa aaaaaaaaaa aatctcccctt tagtgagggt taatttcgcg    60
c                                                                    61

<210> SEQ ID NO 21
<211> LENGTH: 69
<212> TYPE: DNA
<213> ORGANISM: Artificial Sequence
<220> FEATURE:
<223> OTHER INFORMATION: Primer directed to human gene
<220> FEATURE:
<221> NAME/KEY: misc_feature
<222> LOCATION: (40)..(69)
<223> OTHER INFORMATION: n is a, c, g or t; some "n" may be absent so
      that the number of "n" varies between 10-30

<400> SEQUENCE: 21
```

```
ggccagtgaa ttgtattacg acacactata gggaggcggn nnnnnnnnnn nnnnnnnnnn    60 nnnnnnnnn                                                            69

<210> SEQ ID NO 22
<211> LENGTH: 59
<212> TYPE: DNA
<213> ORGANISM: Artificial Sequence
<220> FEATURE:
<223> OTHER INFORMATION: Primer directed to human gene
<220> FEATURE:
<221> NAME/KEY: misc_feature
<222> LOCATION: (30)..(59)
<223> OTHER INFORMATION: n is a, c, g or t; some "n" may be absent so
      that the number of "n" varies between 10-30

<400> SEQUENCE: 22
gcgcgaaatt aaccctcact aaagggagan nnnnnnnnnn nnnnnnnnnn nnnnnnnnn     59

<210> SEQ ID NO 23
<211> LENGTH: 65
<212> TYPE: DNA
<213> ORGANISM: Artificial Sequence
<220> FEATURE:
<223> OTHER INFORMATION: Primer directed to human gene
<220> FEATURE:
<221> NAME/KEY: misc_feature
<222> LOCATION: (40)..(63)
<223> OTHER INFORMATION: t is deoxyribothymidine
<220> FEATURE:
<221> NAME/KEY: misc_feature
<222> LOCATION: (65)..(65)
<223> OTHER INFORMATION: n is a, c, g or t

<400> SEQUENCE: 23
ggccagtgaa ttgtattacg acacactata gggaggcggt tttttttttt tttttttttt    60 tttvn                                                                65

<210> SEQ ID NO 24
<211> LENGTH: 65
<212> TYPE: DNA
<213> ORGANISM: Artificial Sequence
<220> FEATURE:
<223> OTHER INFORMATION: Primer directed to human gene
<220> FEATURE:
<221> NAME/KEY: misc_feature
<222> LOCATION: (1)..(1)
<223> OTHER INFORMATION: n is a, c, g or t
<220> FEATURE:
<221> NAME/KEY: misc_feature
<222> LOCATION: (3)..(26)
<223> OTHER INFORMATION: a is deoxyriboadenosine

<400> SEQUENCE: 24
nbaaaaaaaa aaaaaaaaaa aaaaaaccgc ctccctatag tgtgtcgtaa tacaattcac    60
tggcc                                                                65
```

RESTORATION OF NUCLEIC ACID FROM DEGRADED OR FORMALIN-FIXED AND PARAFFIN-EMBEDDED TISSUE AND USES THEREOF

CROSS-REFERENCE TO RELATED APPLICATIONS

This application is a U.S. national stage entry under 35 U.S.C. §371 of PCT International Patent Application No. PCT/US2007/004892, filed Feb. 26, 2007, and claims priority of U.S. Provisional Patent Application No. 60/778,221, filed Mar. 1, 2006, the contents of which are incorporated herein by reference in their entirety.

FIELD OF THE INVENTION

The invention is directed to methods, oligonucleotides and kits for recovery and restoration of nucleic acid from tissue, in particular tissue where ribonucleic acid has degraded, and formalin-fixed and paraffin-embedded (FFPE) tissue. The approach can be described as complementary-template reverse-transcription (CT-RT) because short single-stranded DNA sequences reverse-transcribed from mRNA are used for the reverse-transcription of complementary sense-RNA templates. The methods can be used to determine patterns of gene expression and chromosomal alterations in archived tissue samples, which may be used for example for identification of early expression of disease-related genes.

BACKGROUND OF THE INVENTION

Throughout this application various publications are referred to in parenthesis. Full citations for these references may be found at the end of the specification immediately preceding the claims. The disclosures of these publications are hereby incorporated by reference in their entireties into the subject application to more fully describe the art to which the subject application pertains.

The development of high-capacity microarrays has enabled the study of thousands of individual transcripts in parallel and helped identify the distinctive transcriptional profiles of tumors (Mohr et al. 2004). Consequently, the hierarchical clustering of tumor profiles has been demonstrated to be valuable for the classification of cancers. One such example has been the classification of gene expression patterns in primary breast tumors, which led to the identification of five distinct tumor subtypes subsequently linked with different clinical outcomes (Perou et al. 2000, Sorlie et al. 2001 and 2003). These studies substantiated the use of molecular taxonomy, in clinical medicine, for cancer diagnosis and identification of suited therapeutic approaches (Golub, 2001; Abramovitz and Leyland-Jones, 2006; Robison et al. 2004; Dietel et al. 2006).

Retrospective transcriptional profiling of archived tissues, which have been linked to long-term outcome of a disease, represent an attractive but challenging approach. The specimens that have been collected in surgical pathology have been routinely formalin-fixed and paraffin-embedded (FFPE), a preservation process that has been shown to induce the formation of cross-linkages between proteins and between proteins and nucleic acids (Werner et al. 2000). This fixation method has detrimental effects on RNA molecules that are only recovered fragmented, chemically modified and in low yields (Krafft et al. 1999; Stanta et al. 1998; Masuda et al. 1999; Coombs et al. 1999; Cronin et al. 2004). Multi-gene retrospective analyses of FFPE-RNA, which have been achieved through in-situ hybridization and relative quantification of target transcripts using real-time polymerase chain reaction (RT-PCR), have remained limited (Lehmann et al. 2001; Lewis et al. 2001; Relf et al. 2002; Capodieci et al. 2005; Paik et al. 2005). Although RT-PCR techniques have been enhanced for the study of larger gene sets, this technique remains impractical for the analysis of tens of thousands of genes and thus identification of early cancer related genes (Cronin et al 2004; Bibikova et al. 2004 a and b; Ma et al. 2006).

One major disadvantage to microarray analysis is the requirement of significant amounts of high-quality RNA, which are essential for increased sensitivity and reproducibility, a characteristic lacking with fragmented FFPE-RNA. Although a few commercial kits have been designed to reliably amplify small amounts of starting material, studies however have suggested that degraded FFPE-RNA is not a good substrate for cDNA synthesis prior to microarray experiments (Masuda et al. 1999; Karsten et al. 2002; Klur et al. 2004; Xiang et al. 2003; Wang et al. 2003). A few reports, describing the high-throughput transcriptional profiling of FFPE-RNA, have not provided any direct correlation with matched frozen tissues and therefore any indication on the percentage of gene retrieval (Onken et al. 2004; Chung et al. 2006).

Considering the high level of degradation of archived RNA, there is a need for a reliable assay for the preparation of highly fragmented and chemically modified FFPE-RNA, prior to in vitro transcription (IVT)-amplification and high-throughput analyses. This problem is solved by the strategy disclosed herein.

SUMMARY OF THE INVENTION

The present invention provides methods of restoring nucleic acid sequences recovered fragmented or degraded from tissues comprising: a) reverse transcribing mRNA from the tissue using random primers or a 5'-promoter-oligo-dT (10-30)-VN-3' primer, or a combination of both, to obtain a RNA/DNA duplex made of mRNA and single-stranded cDNA that is complementary to the mRNA, wherein V is nucleotide A, C, or G; N is nucleotide A, C, G or T; and oligo-dT(10-30) is 10 to 30 deoxyribothymidines; b) removing RNA from the RNA/DNA duplex of step a) to yield a single-stranded cDNA primer that is complementary to the mRNA; c) purifying the single-stranded cDNA primer obtained in step b) to obtain a purified primer; d) hybridizing the purified single-stranded cDNA primer from step c) to a single stranded oligonucleotide to obtain a partially double-stranded oligonucleotide complex with a single-stranded cDNA portion specific to a gene expressed in the tissue, wherein if the primer in step a) is a 5'-promoter-oligo-dT(10-30)-VN-3' primer, then the single stranded oligonucleotide in step d) is 5'-NB-oligo-dA(10-30)-complementary promoter-3', wherein B is nucleotide C, G or T; oligo-dA(10-30) is 10 to 30 deoxyriboadenosines; the number of oligo-dAs is the same as the number of oligo-dTs in the reverse-transcribing primer in step a); and the complementary promoter is complementary to the promoter in step a); and wherein if the primers in step a) are random primers, then the single stranded oligonucleotides in step d) comprise a complementary promoter that is complementary to the promoter in step a), a dideoxynucleotide at their 3' end, and the same numbers of nucleotides as the random primers in step a); e) annealing the single-stranded cDNA portion of the partially double-stranded oligonucleotide complex formed in step d) with sense RNA to form a hybrid product comprising single-stranded sense RNA and cDNA primer that is complementary-bound to the single-stranded sense RNA; f) reverse-transcribing the single-stranded sense RNA of the hybrid product obtained in step e) to extend and restore nucleic acid sequences on the cDNA primer that is complementary-bound to the single-stranded sense RNA to obtain a cDNA/sense RNA duplex; and g) synthesizing double-stranded DNA from the cDNA/sense RNA duplex obtained in step f) so as to obtain a double-stranded DNA that contains a restored nucleic acid sequence from the tissue.

The invention also provides methods of restoring and identifying nucleic acid sequences recovered fragmented or degraded from tissues comprising: a) reverse transcribing mRNA from the tissue using random primers or a 5'-promoter-oligo-dT(10-30)-VN-3' primer, or a combination of both, to obtain a RNA/DNA duplex made of mRNA and single-stranded cDNA that is complementary to the mRNA, wherein V is nucleotide A, C, or G; N is nucleotide A, C, G or T; and oligo-dT(10-30) is 10 to 30 deoxyribothymidines; b) removing RNA from the RNA/DNA duplex of step a) to yield a single-stranded cDNA primer that is complementary to the mRNA; c) purifying the single-stranded cDNA primer obtained in step b) to obtain a purified primer; d) hybridizing the purified single-stranded cDNA primer from step c) to a single stranded oligonucleotide to obtain a partially double-stranded oligonucleotide complex with a single-stranded cDNA portion specific to a gene expressed in the tissue, wherein if the primer in step a) is a 5'-promoter-oligo-dT(10-30)-VN-3' primer, then the single stranded oligonucleotide in step d) is 5'-NB-oligo-dA(10-30)-complementary promoter-3', wherein B is nucleotide C, G or T; oligo-dA(10-30) is 10 to 30 deoxyriboadenosines; the number of oligo-dAs is the same as the number of oligo-dTs in the reverse-transcribing primer in step a); and the complementary promoter is complementary to the promoter in step a); and wherein if the primers in step a) are random primers, then the single stranded oligonucleotides in step d) comprise a complementary promoter that is complementary to the promoter in step a), a dideoxynucleotide at their 3' end, and the same numbers of nucleotides as the random primers in step a); e) annealing the single-stranded cDNA portion of the partially double-stranded oligonucleotide complex formed in step d) to sense nucleic acid templates attached to a surface to form a hybrid product comprising single-stranded sense RNA and cDNA primer that is complementary-bound to the single-stranded sense RNA; and f) incorporating a dye into the hybrid product attached to the surface using DNA or RNA polymerase to form a labeled hybrid product, so as to identify genes that are restored by copy of the template bound to the surface.

The invention further provides methods of restoring nucleic acid sequences recovered fragmented or degraded from tissues comprising: a) obtaining a pool of single stranded cDNA primers that have been synthesized from either degraded or formalin-fixed RNA by reverse-transcription of the RNA; b) creating a double-stranded region on the primer pool with blocking primer 5'-NB-oligo dA (10-30)-complementary-promoter-3' in order to provide a single stranded region for annealing with sense-RNA templates, wherein N is nucleotide A, C, G or T; B is nucleotide C, G or T; oligo-dA(10-30) is 10 to 30 deoxyriboadenosines; and the complementary promoter is complementary to the promoter in the primers in step a); c) annealing the single-stranded cDNA primers with sense RNA to form a hybrid product comprising single-stranded sense RNA and cDNA primer that is complementary-bound to the single-stranded sense RNA; d) reverse-transcribing the single-stranded sense RNA of the hybrid product obtained in step c) to extend and restore nucleic acid sequences on the cDNA primer that is complementary-bound to the single-stranded sense RNA to obtain a cDNA/sense RNA duplex; and e) synthesizing double-stranded DNA from the cDNA/sense RNA duplex obtained in step d) so as to obtain a double-stranded DNA that contains a restored nucleic acid sequence from the tissue.

Also provided are methods of restoring nucleic acid sequences directly onto a solid surface using amplified material obtained from degraded or formalin-fixed and paraffin-embedded RNA, where the method comprises: a) amplifying mRNA containing a poly dA tail from a sample of RNA in order to obtain cRNA; b) reverse-transcribing the cRNA with random primers into single-stranded cDNA primers, where the cDNA has the same orientation as mRNA and carries a poly dA tail; c) binding the cDNA primers to a 5'-biotin-promoter-oligo-dT(10-30)-VN-3' primer attached to microbeads, wherein V is nucleotide A, C, or G; N is nucleotide A, C, G or T; and oligo-dT(10-30) is 10 to 30 deoxyribothymidines; d) synthesizing a DNA strand complementary to the single-stranded cDNA primers directly onto the beads; e) purifying the microbeads from the single-stranded cDNA primers; f) creating a double-stranded region on the elongated primers carried by the microbeads with blocking primer 5'-NB-oligo dA (10-30)-complementary-promoter-3' in order to provide a single stranded region for annealing with sense-RNA templates, wherein N is nucleotide A, C, G or T; B is nucleotide C, G or T; oligo-dA(10-30) is 10 to 30 deoxyriboadenosines; and the complementary promoter is complementary to the promoter in the primers in step c); g) annealing the single-stranded cDNA primers with sense RNA to form a hybrid product comprising single-stranded sense RNA and cDNA primer that is complementary-bound to the single-stranded sense RNA; h) reverse-transcribing the single-stranded sense RNA of the hybrid product obtained in step g) to extend and restore nucleic acid sequences on the cDNA primer, bound to the microbead, that is complementary-bound to the single-stranded sense RNA to obtain a cDNA/sense RNA duplex; and i) synthesizing double-stranded DNA from the cDNA/sense RNA duplex obtained in step h) so as to obtain a double-stranded DNA that contains a restored nucleic acid sequence from the tissue.

Also provided are methods of restoring nucleic acid sequences when starting with a small amount of degraded or formalin-fixed and paraffin-embedded total RNA (below five micrograms of RNA), the method comprising: a) reverse transcribing mRNA from the tissue using T7 or T3 random primers or a 5'-promoter-oligo-dT(10-30)-VN-3' primer, or a combination of both, to obtain a RNA/DNA duplex made of mRNA and single-stranded cDNA that is complementary to the mRNA, wherein V is nucleotide A, C, or G; N is nucleotide A, C, G or T; and oligo-dT(10-30) is 10 to 30 deoxyribothymidines; b) synthesizing double-stranded cDNA duplex using DNA polymerase I in the presence of RNase-H and purifying the double-stranded products on a column; c) increasing the amount of single-stranded DNA sequences, complementary to the messenger RNA, by combining the double-stranded cDNA duplex with 100 nanograms to one micrograms of 5'-promoter-oligo-dT(10-30)-VN-3' primer, or a primer representing a portion of the primer used to reverse-transcribe the mRNA, in the presence of a DNA polymerase for 5-40 cycles of polymerization; d) polymerizing the single-stranded DNA sequences by subjecting the mix obtained in c) to 5 to 40 cycles of about 95 degree Celsius for about 1 minute, about 95 to about 50 degree Celsius for about 1 minute, about 50 degree Celsius for about 2 minutes and about 72 degree Celsius for about 2 minutes; e) purifying the single-stranded DNA from step d); f) hybridizing the purified single-stranded cDNA primer from step e) to a single stranded oligonucleotide to obtain a partially double-stranded oligonucleotide complex with a single-stranded cDNA portion specific to a gene expressed in the tissue, wherein if the primer in step a) is a 5'-promoter-oligo-dT(10-30)-VN-3' primer, then the single stranded oligonucleotide in step i) is 5'-NB-oligo-dA(10-30)-complementary promoter-3', wherein B is nucleotide C, G or T; oligo-dA(10-30) is 10 to 30 deoxyriboadenosines; the number of oligo-dAs is the same as the number of oligo-dTs in the reverse-transcribing primer in step a); and the complementary promoter is complementary to the promoter in step a); and wherein if the primers in step a) are T7 or T3 random primers, then the single stranded oligonucleotides in step f) comprise a complementary promoter that is complementary to the promoter in step a), a dideoxynucleotide at their 3' end, and the same numbers of nucleotides as the random primers in step a); g) annealing the single-stranded cDNA portion of the partially double-stranded oligonucleotide complex formed in step f) to sense nucleic acid templates to form a hybrid product comprising single-stranded sense RNA and cDNA primer that is complementary-bound to the sense nucleic acid; h) reverse-transcribing the single-stranded sense RNA of the hybrid product obtained in step g) to extend and restore nucleic acid sequences onto the cDNA primer that is complementary-bound to the single-stranded sense RNA to obtain a cDNA/sense RNA duplex; and i) synthesizing double-stranded DNA from the cDNA/sense RNA duplex obtained in step g) so as to obtain a double-stranded DNA that contains a restored nucleic acid sequence from the tissue.

The invention provides methods of size exclusion and size selection of a duplex of DNA and RNA obtained from degraded or formalin-fixed and paraffin-embedded (FFPE) tissue, comprising a) reverse transcribing mRNA from the tissue using a 5'-promoter-oligo-dT(10-30)-VN-3' primer to obtain a RNA/DNA duplex of mRNA and single-stranded cDNA that is complementary to the mRNA, wherein V is nucleotide A, C, or G; N is nucleotide A, C, G or T; and oligo-dT(10-30) is 10 to 30 deoxyribothymidines; and b) purifying the RNA/DNA duplex to obtain a duplex of at least 100 basepairs of oligonucleotides.

The invention provides oligonucleotides consisting essentially of 5'-NB-oligo-dA(10-30)-cT7-3' (SEQ ID NO:19) or 5'-NB-oligo-dA(10-30)-cT3-3' (SEQ ID NO:20), wherein N is nucleotide A, C, G or T; B is nucleotide C, G or T; and oligo-dA(10-30) is 10 to 30 deoxyriboadenosines.

The invention also provides pools of single-stranded cDNA oligonucleotide primers that are representative of the 3' region of ribonucleic acid sequences recovered fragmented or degraded from a tissue, where the pool of primers is prepared by a method comprising: a) reverse transcribing mRNA from the tissue using a primer pool comprising random primers or 5'-promoter-oligo-dT(10-30)-VN-3' primers, or a combination of both, to obtain a RNA/DNA duplex made of mRNA and single-stranded cDNA that is complementary to the mRNA, wherein V is nucleotide A, C, or G; N is nucleotide A, C, G or T; and oligo-dT(10-30) is 10 to 30 deoxyribothymidines; and wherein the primer pool comprises sequences that represent genes transcribed in the tissue; b) removing RNA from the RNA/DNA duplex of step a) to yield a single-stranded cDNA primer that is complementary to the mRNA; and c) purifying the single-stranded cDNA primer obtained in step b to obtain a purified primer pool representative of messenger RNAs that have been transcribed by the tissue.

The invention further provides kits for restoring nucleic acid from tissue comprising any of the oligonucleotides of the invention.

BRIEF DESCRIPTION OF THE FIGURES

FIG. 4A-4B. The size of single-stranded DNA transcripts is determined by PCR analysis. (A) The cDNAs of three genes, cyclin D1 (Ccnd1), tumor protein 53 (p53) and human tyrosine-kinase type-receptor (Her-2/neu) are represented. The name, size and accession number of the dsDNA coding for each gene is indicated on the left of the cDNAs. Three forward primers (black arrows from left to right), for each gene, are positioned on the upper side of the line representing each cDNA. The reverse primers (black arrow from left to right), for each gene, are positioned on the lower side of the line that represents the cDNA. The primers were designed to target the 3'end of Ccnd1, p53 and Her-2. For Ccnd1, forward primers (from the right to the left) were combined with the reverse primer to obtain primer pairs 1, 2 and 3, which generated. PCR products of 87, 126 and 251 base pairs, respectively. For p53 the PCR products generated by primer-pairs 4, 5 and 6 have a size of 77, 133 and 214 base pairs, respectively. For Her-2, the PCR products from primer-pairs 7, 8 and 9 have a size of 72, 161 and 225 base pairs, respectively. (B) Size distribution on a 1% agarose gel of the PCR products obtained when using different populations of dsDNA. The first lane of each gel displays the ladder (500, 400, 300, 200 and 100 bp from top to bottom of gel). Lanes 1-9 show the PCR products from the primer-pairs 1-3 for Ccnd1, 4-6 for p53 and 7-9 for Her-2. PCR experiments were performed with no DNA (panel 1), dsDNA generated from UHR RNA (panel 2), dsDNA obtained from 10 year-old frozen RNA (panel 3), dsDNA obtained from 10 year-old FFPE-RNA (panel 4) and dsDNA generated by CT-RT (panel 5).

FIG. 7A-7C. Restoration of single-stranded DNA primers obtained from colon and breast cancer samples using the same sense-RNA template library. (A) Scatter plot representing the $\log_{10}$ of the correlation between experimental repeats after restoration and IVT-amplification of four year-old FFPE-RNA from a colon sample. The determination coefficient is indicated in the top left corner, $R^2=0.942$. (B) Scatter plot displaying the linear correlation between two technical repeats obtained after restoration and IVT-amplification of 8 year-old FFPE-RNA from breast tissue. The determination coefficient is indicated in the top left corner, $R^2=0.9147$. (C) The $\log_2$ ratios of 60 genes that were detected after restoration in either or both colon and breast samples were sorted on a heat map. Five micrograms of cRNA obtained after IVT-amplification of restored colon and breast RNA were labeled and hybridized on 8,000 features cDNA microarrays. For each tissue, 20 genes were selected that showed specific expression in either colon or breast FFPE samples and sorted them by descending order (40 genes total). For both tissues, 20 common genes were selected and placed between the tissue specific genes. For each tissue, duplicate measures were performed and the $\log_2$ of the mean ratios represented. The Genebank accession numbers are displayed on the right of the panel. Genes listed in text with light shading have been previously identified for each tissue.

DETAILED DESCRIPTION OF THE INVENTION

Figure 1:
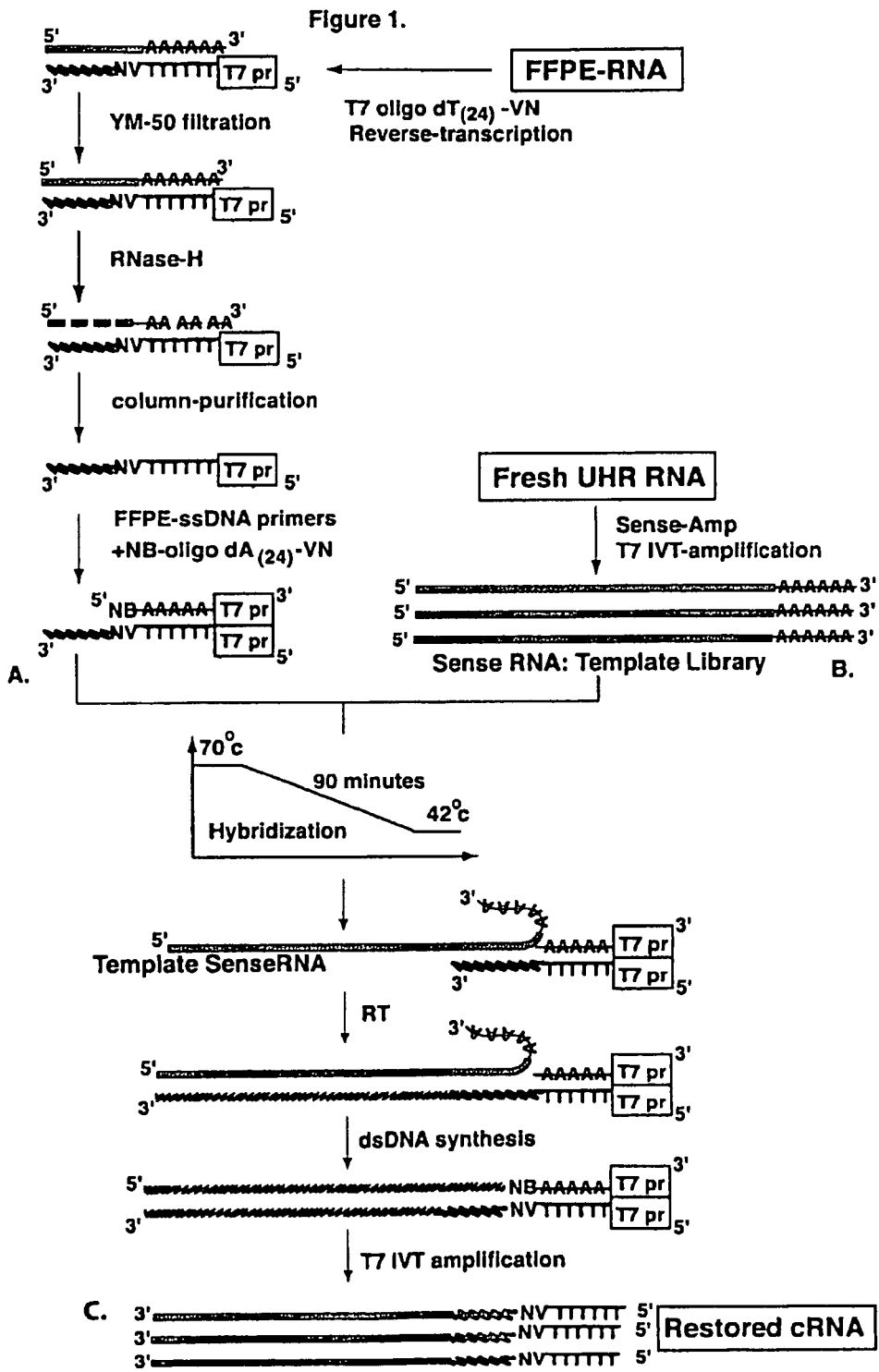
FIG. 1A-1C. Restoration of single-stranded DNAs obtained from FFPE-RNA: Complementary-Template Reverse-Transcription (CT-RT). (A) The RNA extracted from FFPE tissue is reverse-transcribed using an anchored 5'-T7-oligo-dT(24)-NV-3' primer. The mRNA/cDNA duplex is filtered on a YM-50 column, single-stranded with RNase-H and purified. The 5'-NB-Oligo-dA(24)-cT7-3' (SEQ ID NO:24) (complementary to the T7 promoter) is annealed to the FFPE-cDNA primers to prevent non-specific binding of oligo-dT$_{24}$ to polyA tailed of sense-RNA templates. (B) Total RNA from universal human reference (UHR, Stratagene) is amplified using the Sense-Amp cRNA amplification kit from Genisphere in order to obtain Sense-RNA with the same orientation as messenger RNA (Goff et al. 2004). (C) Single-stranded DNA primers are hybridized to their sense-RNA template between seventy and forty-two degree Celsius for 90 minutes. The hybridized products are reverse-transcribed by a process described as Complementary-Template Reverse-Transcription (CT-RT). The restored FFPE-cDNAs are doubled stranded and transcribed in-vitro using T7 polymerase.

The present invention is directed to methods, oligonucleotides and kits for recovery and restoration of nucleic acid from tissue, in particular from degraded tissue and formalin-fixed and paraffin-embedded (FFPE) tissue, as described herein.

As used herein, "degraded" tissue means tissue in which the nucleic acid is fragmented and/or chemically modified.

The standard abbreviations for nucleotide bases are used as follows: adenine (A), cytosine (C), guanine (G), thymine (T) and uracil (U); the letters "A", "C", "G", "T" and "U" are also used to represent the whole nucleotide containing the respective base. "dT" means deoxyribothymidine; "dA" means deoxyriboadenosine; and "ddN" means dideoxynucleotide. The "3'" end of an oligonucleotide has a free hydroxyl group at the 3' carbon of a sugar in the oligonucleotide. The "5'" end of an oligonucleotide has a free hydroxyl or phosphate group at the 5' carbon of a sugar in the oligonucleotide. "Complementary" nucleotides or nucleic acid sequences are those that can form a perfect base pair, where "A" pairs with "T" or "U", and "C" pairs with "G".

As used herein, "anneal" or "annealing" is a biochemical process by which two complementary nucleic acid strands are bound together at an optimal temperature so as to form perfect base pairs. "Hybridization" means the association of two complementary nucleic acid strands to form a double stranded molecule. The hybrids can contain two deoxyribonucleic acid (DNA) strands, two ribonucleic acid (RNA) strands, or a DNA strand and a RNA strand.

"Sense" RNA refers to RNA that contains a coding region that can be translated to produce a polypeptide. Sense RNA sequences are in the same orientation as messenger RNA (mRNA) sequences obtained from tissue. "Complementary RNA" (cRNA) or anti-sense RNA refers to RNA that is a complementary copy of normal or "sense" messenger RNA. "Complementary DNA" (cDNA) refers to DNA that is a complementary copy of normal or "sense" messenger RNA. "Reverse transcription" or "reverse transcribing" means a process by which single stranded DNA (ssDNA) is copied from RNA using the enzyme reverse transcriptase.

Sequences for specific promoters are:

```
sense T7,
                                    (SEQ ID NO: 13)
5'-GGCCAGTGAATTGTATTACGACACACTATAGGGAGGCGG-3';

complementary (antisense) T7 (cT7),
                                    (SEQ ID NO: 14)
5'-CCGCCTCCCTATAGTGTGTCGTAATACAATTCACTGGCC-3';

sense T3,
                                    (SEQ ID NO: 15)
5'-GCGCGAAATTAACCCTCACTAAAGGGAGA-3';

complementary (antisense) T3 (cT3),
                                    (SEQ ID NO: 16)
5'-TCTCCCTTTAGTGAGGGTTAATTTCGCGC-3'.
```

"Random primer" are oligonucleotides of at least 8 nucleotides in length that can represent all possible combinations of sequences. Random primers are usually 8-15 nucleotides in length and typically less than 100 oligonucleotides. The random primer can be combined with a promoter (e.g., 5'-promoter-random primer-3'). Preferred promoter-random primers include the T3 or T7 promoter and at least 8 additional nucleotides.

As used herein, a "blocking primer" is a primer designed to bind a specific sequence that is present on all of the primers represented in a primer pool. This sequence being complementary allows the single stranded sequence, which is specific to a gene expressed in the tissue, to find its complementary sense-RNA transcript, without interaction with the poly dA tail. Because of the blocking primer, the oligo dT present on the primers will not bind non-specifically any sense-RNA transcripts.

The invention provides a method of restoring nucleic acid sequences recovered fragmented or degraded from a tissue comprising:

a) reverse transcribing mRNA from the tissue using random primers or a 5'-promoter-oligo-dT(10-30)-VN-3' primer, or a combination of both, to obtain a RNA/DNA duplex made of mRNA and single-stranded cDNA that is complementary to the mRNA, wherein V is nucleotide A, C, or G; N is nucleotide A, C, G or T; and oligo-dT(10-30) is 10 to 30 deoxyribothymidines;

b) removing RNA from the RNA/DNA duplex of step a) to yield a single-stranded cDNA primer that is complementary to the mRNA;

c) purifying the single-stranded cDNA primer obtained in step b) to obtain a purified primer;

d) hybridizing the purified single-stranded cDNA primer from step c) to a single stranded oligonucleotide to obtain a partially double-stranded oligonucleotide complex with a single-stranded cDNA portion specific to a gene expressed in the tissue, wherein if the primer in step a) is a 5'-promoter-oligo-dT (10-30)-VN-3' primer, then the single stranded oligonucleotide in step d) is 5'-NB-oligo-dA(10-30)-complementary promoter-3', wherein B is nucleotide C, G or T; oligo-dA(10-30) is 10 to 30 deoxyriboadenosines; the number of oligo-dAs is the same as the number of oligo-dTs in the reverse-transcribing primer in step a); and the complementary promoter is complementary to the promoter in step a); and wherein if the primers in step a) are random primers, then the single stranded oligonucleotides in step d) comprise a complementary promoter that is complementary to the promoter in step a), a dideoxynucleotide at their 3' end, and the same numbers of nucleotides as the random primers in step a);

e) annealing the single-stranded cDNA portion of the partially double-stranded oligonucleotide complex formed in step d) with sense RNA to form a hybrid product comprising single-stranded sense RNA and cDNA primer that is complementary-bound to the single-stranded sense RNA;

f) reverse-transcribing the single-stranded sense RNA of the hybrid product obtained in step e) to extend and restore nucleic acid sequences on the cDNA primer that is complementary-bound to the single-stranded sense RNA to obtain a cDNA/sense RNA duplex; and g) synthesizing double-stranded DNA from the cDNA/sense RNA duplex obtained in step f) so as to obtain a double-stranded DNA that contains a restored nucleic acid sequence from the tissue.

The double-stranded DNA (dsDNA) in step g) comprises restored nucleic acid sequences from genes transcribed in the tissue. The synthesis of double-stranded DNA from a cDNA/sense RNA duplex, such as in step g), can be carried out using DNA polymerase in the presence of RNase-H. The double-stranded DNA can comprise a promoter for in vitro transcription of the double-stranded DNA or polymerase chain reaction amplification. The double-stranded DNA can be transcribed in vitro to obtain RNA that is complementary (cRNA) to the mRNA originally obtained from the tissue. Preferably, transcription is carried out in vitro. In vitro transcription amplification can be carried out using T7 or T3 RNA polymerase.

The sense nucleic acid template that is used to form a hybrid product comprising a single-stranded sense RNA, DNA or double-stranded DNA, and cDNA primer can be attached to a surface, such as, for example, a glass or glass-coated surface, microbeads or a column. The microbeads can subsequently be used as is or attached onto a glass slide or a surface that keeps them individually separated. Restoration of nucleic acid sequences can be carried out on the surface to which the sense nucleic acid is attached. The restoration process can include insertion of labeling molecules, which can be quantified directly on the surface, for example, by an antibody or fluorescence. After restoration of the nucleic acid sequence, the surface can be heated to free elongated and restored primers for analysis on a microarray, or if the surface is the microarray, the step of restoration can be performed directly onto the nucleic acid template attached to the surface.

A dye label can be incorporated into restored nucleic acid molecules. The dye can be, for example, Cyanine-3, Cyanine-5, amino-allyl or biotin. Cyanine-3 or Cyanine-5 d-NTP, amino-allyl dNTP or biotin labelled dNTPs can be used, for example, when the nucleic acid template attached to the glass or beads is a sense-RNA, a single-stranded sense-DNA or double-stranded DNA, and can be incorporated into the restored nucleic acid molecules, which are synthesized directly onto the surface, e.g., glass slide or beads.

The invention also provides a method of restoring and identifying nucleic acid sequences recovered fragmented or degraded from a tissue comprising:

a) reverse transcribing mRNA from the tissue using random primers or a 5'-promoter-oligo-dT(10-30)-VN-3' primer, or a combination of both, to obtain a RNA/DNA duplex made of mRNA and single-stranded cDNA that is complementary to the mRNA, wherein V is nucleotide A, C, or G; N is nucleotide A, C, G or T; and oligo-dT(10-30) is 10 to 30 deoxyribothymidines;

b) removing RNA from the RNA/DNA duplex of step a) to yield a single-stranded cDNA primer that is complementary to the mRNA;

c) purifying the single-stranded cDNA primer obtained in step b) to obtain a purified primer;

d) hybridizing the purified single-stranded cDNA primer from step c) to a single stranded oligonucleotide to obtain a partially double-stranded oligonucleotide complex with a single-stranded cDNA portion specific to a gene expressed in the tissue, wherein if the primer in step a) is a 5'-promoter-oligo-dT (10-30)-VN-3' primer, then the single stranded oligonucleotide in step d) is 5'-NB-oligo-dA(10-30)-complementary promoter-3', wherein B is nucleotide C, G or T; oligo-dA(10-30) is 10 to 30 deoxyriboadenosines; the number of oligo-dAs is the same as the number of oligo-dTs in the reverse-transcribing primer in step a); and the complementary promoter is complementary to the promoter in step a); and wherein if the primers in step a) are random primers, then the single stranded oligonucleotides in step d) comprise a complementary promoter that is complementary to the promoter in step a), a dideoxynucleotide at their 3' end, and the same numbers of nucleotides as the random primers in step a);

e) annealing the single-stranded cDNA portion of the partially double-stranded oligonucleotide complex formed in step d) to sense nucleic acid templates attached to a surface to form a hybrid product comprising single-stranded sense RNA or DNA or double-stranded DNA, and cDNA primer that is complementary-bound to the sense nucleic acid; and f) incorporating a dye into the hybrid product attached to the surface using DNA or RNA polymerase to form a labeled hybrid product, so as to identify genes that are restored by copy of the template bound to the surface.

The primer in step a) can comprise a primer pool having sequences that represent genes transcribed in the tissue, and the purified primer in step c) can comprise a purified primer pool representative of messenger RNAs that have been transcribed by the tissue. This primer pool can also be obtained using random primers through reverse-transcription of complementary RNA (cRNA) obtained by in-vitro-amplification of degraded or formalin-fixed and paraffin-embedded RNA. The resulting primer pool carrying an oligo dT(10-30) is annealed to a oligo dA (10-30) and then annealed to the nucleic acid templates represented onto the surface for reverse-transcription or DNA synthesis using either RNA or DNA polymerases.

In the methods disclosed herein, the sense RNA or sense nucleic acid templates can be obtained from a reference RNA library, for example from the universal human reference (UHR) library (Stratagene), from RNA obtained from a specific organ, from RNA from a specific stage of development, from RNA extracted from a mix of different types of cancer tissues or cells, from RNA extracted from different types of cancers originating from the same tissue, or from RNA obtained from a mix of different types of tissues affected by the same disease or by different diseases.

Sense RNA can be obtained by in vitro transcription of a T7 or T3 promoter incorporated into the 3' end of cDNA to provide sense RNA with the same orientation as mRNA. The sense RNA can be obtained by template-switch of messenger-RNA, and inclusion of a primer in the 3' region of the transcripts. The primer may be extended by PCR experiments with a promoter, which provides the 5' promoter necessary for IVT-amplification and synthesis of sense-RNA templates. The sense-RNA library may also be obtained by purification of poly dA messenger RNA extracted from cell lines, or tissues and then used for the CT-RT process. The purification of poly dA RNA from different sources provides the different templates necessary for CT-RT.

In the methods described herein, the RNA/DNA duplex of mRNA and single-stranded cDNA can be purified before removing RNA from the RNA/DNA duplex. Purification can yield a RNA/DNA duplex of at least 100 basepairs of oligonucleotides. Preferably, at least 65 nucleotides are from the primer. Preferably, at least 35 nucleotides are from the mRNA. Purification can be used to exclude nucleic acid fragments shorter than 75 nucleotides and to exclude primers that have not been used for reverse-transcription of fragmented polyA messenger RNA. Purification can eliminate single-stranded primer and short double strands of DNA and RNA, wherein the RNA comprises a poly A tail and less than 10 nucleotides of genetic information. The RNA/DNA duplex can be purified, for example, using a size exclusion column or electromagnetic beads to which the primer is attached or by migration through an electric field that allows separation of RNA/DNA duplexes of different sizes. The RNA/DNA duplex can be purified with a YM50 filter or with a YM100 filter to obtain a RNA/DNA duplex larger than 100 basepairs. The RNA/DNA duplex can be purified by electrophoresis through a polyacrylamide gel to obtain a RNA/DNA duplex larger than 75 basepairs.

In the methods disclosed herein, the primers can be a 5'-promoter-oligo-dT(10-30)-VN-3' primer, such as, for example, 5'-T7-oligo-dT(10-30)-VN-3' (SEQ ID NO:17) or 5'-T3-oligo-dT(10-30)-VN-3' (SEQ ID NO:18), where V is nucleotide A, C, or G; N is nucleotide A, C, G or T; and oligo-dT(10-30) is 10 to 30 deoxyribothymidines. Preferably, dT(10-30) is dT(15-25) or dT(24).

The random primers can be 5'-promoter-oligo-N(10-30)-3' primers, such as, for example, 5'-T7-oligo-N(10-30)-3' (SEQ ID NO:21) or 5'-T3-oligo-N(10-30)-3' (SEQ ID NO:22), where oligo-N(10-30) is 10 to 30 N, and N is nucleotide A, C, T or G. Preferably, N(10-30) is N(15-25) or N(24). The random primers can be a mix of random primers, where the random primers comprise, for example, T3 or T7 promoter and at least 8 additional nucleotides.

In the methods disclosed herein, RNA can be removed from the RNA/DNA duplex in using RNase-H to digest the RNA or using a deoxyribozyme that specifically cleaves RNA strands leaving DNA intact. The method can further comprise using boiling and thawing to remove digested RNA from the DNA after RNase-H digestion.

Single-stranded DNA primer, such as obtained after removal of RNA from the RNA/DNA duplex, can be purified, for example, using a purification column, using electromagnetic beads to which the primer is attached, or by electrophoresis through a polyacrylamide gel.

Once the single-stranded DNA primer pool has been synthesized and purified from degraded or formalin-fixed and paraffin-embedded mRNA, it can be hybridized to the sense nucleic acid templates, in order to obtain a partially double-stranded oligonucleotide complex with a single-stranded DNA portion specific to a gene expressed in the tissue. The hybridization of complementary sequences can be obtained by incubating the partially-double-stranded DNA primer pool with the sense nucleic acid sequences at about seventy degrees Celsius for about 10 minutes and then about ninety minutes between about 70 and about 42 degree Celsius. The slow decrease in temperature allows for the recognition of complementary sequences. When the primer pool is obtained by reverse-transcription with random primers of cRNA obtained by in-vitro transcription amplification of degraded or formalin-fixed and paraffin embedded RNA, the hybridization can be obtained by incubating at about 42 degree Celsius for several hours. Once the hybridization step is completed, the reverse-transcription of sense RNA templates or the synthesis of DNA by copy of sense-DNA templates or double-stranded DNA templates allows for restoration of transcripts indirectly or directly onto a solid surface.

In one version of the methods disclosed herein, the promoter in the primer used in step a) is T7 (SEQ ID NO:13) and the complementary promoter used in the single stranded oligonucleotide in step d) is cT7 (SEQ ID NO: 14). In another version, the promoter in step a) is T3 (SEQ ID NO:15) and the complementary promoter in step d) is cT3 (SEQ ID NO:16). The random primers in step a) can comprise 5'-promoter-oligo-N(10-30)-3' primers and the single stranded oligonucleotides in step d) can comprise 5'-complementary promoter-oligo-N(10-30)-ddN-3', wherein oligo-N(10-30) is 10 to 30 N, wherein N is nucleotide A, C, T or G, and wherein ddN is a dideoxynucleotide. Preferably, N(10-30) is N(15-25) or N(24).

In the methods disclosed herein, the mRNA can be from tissue that has been archived and formalin-fixed, such as formalin-fixed and paraffin-embedded (FFPE) tissue. The mRNA can be degraded and obtained from tissue that has been frozen, that has been stored in a refrigerator, that has been recovered from a cadaver for forensic analysis, or that has been recovered from a source of preserved tissue that has not been preserved by formaldehyde fixation.

Also provided is a method of restoring nucleic acid sequences recovered fragmented or degraded from a tissue comprising:

a) obtaining a pool of single stranded cDNA primers that have been synthesized from either degraded or formalin-fixed RNA by reverse-transcription of the RNA;

b) creating a double-stranded region on the primer pool with blocking primer 5'-NB-oligo dA (10-30)-complementary-promoter-3' in order to provide a single stranded region for annealing with sense-RNA templates, wherein N is nucleotide A, C, G or T; B is nucleotide C, G or T; oligo-dA(10-30) is 10 to 30 deoxyriboadenosines; and the complementary promoter is complementary to the promoter in the primers in step a);

c) annealing the single-stranded cDNA primers with sense RNA to form a hybrid product comprising single-stranded sense RNA and cDNA primer that is complementary-bound to the single-stranded sense RNA;

d) reverse-transcribing the single-stranded sense RNA of the hybrid product obtained in step c) to extend and restore nucleic acid sequences on the cDNA primer that is complementary-bound to the single-stranded sense RNA to obtain a cDNA/sense RNA duplex; and e) synthesizing double-stranded DNA from the cDNA/sense RNA duplex obtained in step d) so as to obtain a double-stranded DNA that contains a restored nucleic acid sequence from the tissue.

The primers in step a) can comprise, for example, a T7 promoter and the complementary promoter in step b) is cT7. The primers in step a) can comprise a T3 promoter and the complementary promoter in step b) is cT3.

Synthesis of the double-stranded DNA from the cDNA/sense RNA duplex can be carried out using DNA polymerase in the presence of RNase-H. The double-stranded DNA can comprise a promoter for transcription of the double-stranded DNA. The double-stranded DNA can be transcribed in vitro to obtain RNA that is complementary (cRNA) to the mRNA of step a). The transcription can be carried out in vitro using T7 or T3 RNA polymerase.

Also provided is a method of restoring nucleic acid sequences directly onto a solid surface using amplified material obtained from degraded or formalin-fixed and paraffin-embedded RNA, where the method comprises:

a) amplifying mRNA containing a poly dA tail from a sample of RNA in order to obtain cRNA;

b) reverse-transcribing the cRNA with random primers into single-stranded cDNA primers, where the cDNA has the same orientation as mRNA and carries a poly dA tail;

c) binding the cDNA primers to a 5'-biotin-promoter-oligo-dT(10-30)-VN-3' primer attached to microbeads, wherein V is nucleotide A, C, or G; N is nucleotide A, C, G or T; and oligo-dT(10-30) is 10 to 30 deoxyribothymidines;

d) synthesizing a DNA strand complementary to the single-stranded cDNA primers directly onto the beads;

e) purifying the microbeads from the single-stranded cDNA primers;

f) creating a double-stranded region on the elongated primers carried by the microbeads with blocking primer 5'-NB-oligo dA (10-30)-complementary-promoter-3' in order to provide a single stranded region for annealing with sense-RNA templates, wherein N is nucleotide A, C, G or T; B is nucleotide C, G or T; oligo-dA(10-30) is 10 to 30 deoxyriboadenosines; and the complementary promoter is complementary to the promoter in the primers in step c);

g) annealing the single-stranded cDNA primers with sense RNA to form a hybrid product comprising single-stranded sense RNA and cDNA primer that is complementary-bound to the single-stranded sense RNA;

h) reverse-transcribing the single-stranded sense RNA of the hybrid product obtained in step g) to extend and restore nucleic acid sequences on the cDNA primer, bound to the microbead, that is complementary-bound to the single-stranded sense RNA to obtain a cDNA/sense RNA duplex; and i) synthesizing double-stranded DNA from the cDNA/sense RNA duplex obtained in step h) so as to obtain a double-stranded DNA that contains a restored nucleic acid sequence from the tissue.

The method can further comprise using the promoter contained in the double-stranded DNA, attached to the microbeads, to perform a T7 or T3 amplification in order to obtain restored cRNA for microarray analysis. The method has the advantage that the RNA sample in step a) can contain, in addition to mRNA, transfer RNA, ribosomal RNA, and/or microRNA. The cRNA obtained in step a) can be in microgram quantities. In step e) the microbeads can be purified from the single-stranded cDNA primers by incubating them in a solution of 0.1M NaOH. The microbeads, which carry a piece of sequence specific to the genes expressed in the tissue, can be purified magnetically.

Also provided is a method of restoring nucleic acid sequences when starting with a small amount of degraded or formalin-fixed and paraffin-embedded total RNA (below five micrograms of RNA), the method comprising:

a) reverse transcribing mRNA from the tissue using T7 or T3 random primers or a 5'-promoter-oligo-dT(10-30)-VN-3' primer, or a combination of both, to obtain a RNA/DNA duplex made of mRNA and single-stranded cDNA that is complementary to the mRNA, wherein V is nucleotide A, C, or G; N is nucleotide A, C, G or T; and oligo-dT(10-30) is 10 to 30 deoxyribothymidines;

b) synthesizing double-stranded cDNA duplex using DNA polymerase I in the presence of RNase-H and purifying the double-stranded products on a column;

c) increasing the amount of single-stranded DNA sequences, complementary to the messenger RNA, by combining the double-stranded cDNA duplex with 100 nanograms to one micrograms of 5'-promoter-oligo-dT(10-30)-VN-3' primer in the presence of a DNA polymerase for 5-40 cycles of polymerization;

d) polymerizing the single-stranded DNA sequences by subjecting the mix obtained in c) to 4 to 40 cycles of 95 degree Celsius for 1 minute, 95 to 50 degree Celsius for 1 minute, 50 degree Celsius for 2 minutes and 72 degree Celsius for 2 minutes;

e) purifying the single-stranded DNA from step d);

f) hybridizing the purified single-stranded cDNA primer from step e) to a single stranded oligonucleotide to obtain a partially double-stranded oligonucleotide complex with a single-stranded cDNA portion specific to a gene expressed in the tissue, wherein if the primer in step a) is a 5'-promoter-oligo-dT (10-30)-VN-3' primer, then the single stranded oligonucleotide in step f) is 5'-NB-oligo-dA(10-30)-complementary promoter-3', wherein B is nucleotide C, G or T; oligo-dA(10-30) is 10 to 30 deoxyriboadenosines; the number of oligo-dAs is the same as the number of oligo-dTs in the reverse-transcribing primer in step a); and the complementary promoter is complementary to the promoter in step a); and wherein if the primers in step a) are T7 or T3 random primers, then the single stranded oligonucleotides in step f) comprise a complementary promoter that is complementary to the promoter in step a), a dideoxynucleotide at their 3' end, and the same numbers of nucleotides as the random primers in step a);

g) annealing the single-stranded cDNA portion of the partially double-stranded oligonucleotide complex formed in step t) to sense nucleic acid templates to form a hybrid product comprising single-stranded sense RNA and cDNA primer that is complementary-bound to the sense nucleic acid;

h) reverse-transcribing the single-stranded sense RNA of the hybrid product obtained in step g) to extend and restore nucleic acid sequences onto the cDNA primer that is complementary-bound to the single-stranded sense RNA to obtain a cDNA/sense RNA duplex; and i) synthesizing double-stranded DNA from the cDNA/sense RNA duplex obtained in step g) so as to obtain a double-stranded DNA that contains a restored nucleic acid sequence from the tissue.

The double-stranded DNA (dsDNA) in step i) comprises restored nucleic acid sequences from genes transcribed in the tissue. The synthesis of double-stranded DNA from a cDNA/sense RNA duplex can be carried out using DNA polymerase in the presence of RNase-H. The double-stranded DNA can comprise a promoter for in vitro transcription of the double-stranded DNA. The double-stranded DNA can be transcribed in vitro to obtain RNA that is complementary (cRNA) to the mRNA originally obtained from the tissue. Preferably, transcription is carried out in vitro. In vitro transcription amplification can be carried out using T7 or T3 RNA polymerase. The single-stranded DNA products obtained by polymerization can be purified in step e) on a size exclusion column that allows purification of fragments larger than 100 nucleotides. The resulting products can then be purified on a filter and eluted for hybridization to the sense-RNA library. In the method disclosed herein, when starting with a small amount of starting material, the single-stranded DNA primers obtained from step e) can be annealed to the blocking primer prior to being hybridized to sense nucleic acid templates attached to a solid surface. Once hybridized to their target templates the single-stranded DNA primers with a double stranded region can be elongated directly onto the surface, in the presence of a dye or a molecule attached to the dNTPs that can be quantified.

In the methods disclosed herein, use of 5'-NB-oligo-dA (10-30)-complementary promoter-3' to obtain a partially double-stranded oligonucleotide complex prevents non-specific binding of oligo-dT(10-30) to the polyA tail of random sense-RNA templates represented in a sense-RNA template library.

Modified random primers complementary promoter-3'dd, which contain a 3' dideoxyribonucleotide (dd) or a modification preventing extension of the primer, to obtain a partially double stranded oligonucleotide complex, can be used to prevent non-specific binding of random primers, used for reverse-transcription of formalin-fixed and paraffin-embedded (FFPE) RNA, to random sense-RNA templates. The modified random primers are unable to reverse-transcribe sense-RNA templates in the presence of a reverse-transcriptase, allowing only the T7 or T3 random primers, which contain sequences complementary to the mRNA, to reverse-transcribe the sense-RNA templates.

A blocking primer made of RNA or DNA can be used that has one or more mutations in the complementary promoter region to prevent amplification of short sequences or mutated sequences obtained from formalin-fixed- and paraffin-embedded (FFPE) RNA that have not bound to a sense-RNA template. Sequences that would not find a sense-RNA template, because of the double stranded promoter and the poly dA and poly dT, would produce an excessive amount of poly dA sequences during in vitro amplification, and thus dilute the restored information. Only sequences that are being double-stranded will remove the RNA primer which contains the mutations that disable the promoter activity.

In the method disclosed herein, the step of annealing the single-stranded cDNA with sense RNA is preferably carried out at a temperature that changes from about 70° C. to about 42° C. over a period of at least 10 minutes. More preferably, the temperature change occurs over a period of at least 30 minutes or over a period of about 90 minutes. Alternatively, the sense-RNA library could be heated at about 70° C. for about 10 minutes and then placed on ice prior to addition of the single-stranded DNA primer pool, which contains a double-stranded portion. The single-stranded DNA primer pool may be added to the sense-RNA library and incubated for at least 10 minutes, but preferably 30 minutes or over a period of 90 minutes at temperatures that may vary between about 25° C. and about 50° C. The higher the temperature, the higher the stringency and the less short single-stranded DNA transcripts may find their complementary sense-RNA templates.

The invention also provides a method of size exclusion and size selection of a duplex of DNA and RNA obtained from degraded or formalin-fixed and paraffin-embedded (FFPE) tissue, comprising a) reverse transcribing mRNA from the tissue using a 5'-promoter-oligo-dT(10-30)-VN-3' primer to obtain a RNA/DNA duplex of mRNA and single-stranded cDNA that is complementary to the mRNA, wherein V is nucleotide A, C, or G; N is nucleotide A, C, G or T; and oligo-dT(10-30) is 10 to 30 deoxyribothymidines; and b) purifying the RNA/DNA duplex to obtain a duplex of at least 100 basepairs of oligonucleotides. Preferably, at least 65 nucleotides are from the primer. Preferably, at least 35 nucleotides are from the mRNA.

The invention provide an oligonucleotide consisting essentially of 5'-NB-oligo-dA(10-30)-cT7-3' (SEQ ID NO:19) and an oligonucleotide consisting essentially of 5'-NB-oligo-dA(10-30)-cT3' (SEQ ID NO:20), wherein N is nucleotide A, C, G or T; B is nucleotide C, G or T; and oligo-dA(10-30) is 10 to 30 deoxyriboadenosines. Preferably, oligo-dA(10-30) is oligo-dA(15-25) or oligo-dA(24).

The invention also provides a pool of single-stranded cDNA oligonucleotide primers with a double-stranded region that are representative of the 3' region of ribonucleic acid sequences recovered fragmented or degraded from a tissue, where the pool of primers is prepared by a method comprising:

a) reverse transcribing mRNA from the tissue using a primer pool comprising random primers or 5'-promoter-oligo-dT(10-30)-VN-3' primers, or a combination of both, to obtain a RNA/DNA duplex made of mRNA and single-stranded cDNA that is complementary to the mRNA, wherein V is nucleotide A, C, or G; N is nucleotide A, C, G or T; and oligo-dT(10-30) is 10 to 30 deoxyribothymidines; and wherein the primer pool comprises sequences that represent genes transcribed in the tissue;

b) removing RNA from the RNA/DNA duplex of step a) to yield a single-stranded cDNA primer that is complementary to the mRNA; and c) purifying the single-stranded cDNA primer obtained in step b to obtain a purified primer pool representative of messenger RNAs that have been transcribed by the tissue. Preferably, the RNA/DNA duplex is purified after step a) and before step b).

The invention also provides kits for restoring nucleic acid from tissue, where the kits comprise any of the oligonucleotides disclosed herein. The kit can further comprise a sense RNA library, for example, a sense-RNA library that has been designed for work with degraded material from a specific tissue, such as normal tissue or a cancerous tissue, for example breast tissue or colon tissue. The sense-RNA library can be attached to a surface, such as a glass surface, microbeads or a column. The sense-RNA library can be composed of sense-RNA directly related to the single-stranded DNA primer pool. The sense-RNA library can be composed of an excess of sense-RNA templates for each gene of a subject. The sense-RNA library can be obtained by amplification of cDNAs that contain a promoter in the 5' end. The sense-RNA library can contain transcripts that are related to a disease that has affected the degraded or formalin-fixed and paraffin-embedded tissue and/or the sense-RNA library can contain transcripts from different classes of cancers that have been identified for a specific tissue. The kit can also comprise DNA polymerase, RNase H, and buffers compatible with reverse-transcriptases.

The methods, oligonucleotides, and kits disclosed herein can provide increased nucleic acid sequences for identification of genes expressed in tissue by microarray analysis. The methods disclosed herein can be used to determine the pattern of gene expression (mRNA expression) and chromosomal alterations (copy number, heterozygosity) in archived tissue samples. Disease-related genes that are expressed in a subject can be identified following restoration of nucleic acid sequences from a tissue sample from the subject using any of the methods disclosed herein. Such diseases include, for example, cancer such as breast cancer or colon cancer, virus-related cancer, a type of flu, or a viral, bacterial, genetic and degenerative disease. The subject can be, for example, a mouse, rat, cat, dog, horse, sheep, cow, steer, bull, livestock, or monkey or other primate. Preferably, the subject is a human. In tissue from subjects having an infection, the methods can be used to determine the pattern of gene expression of the pathogen (e.g., virus, bacteria, fungus) causing the infection.

This invention will be better understood from the Experimental Details, which follow. However, one skilled in the art will readily appreciate that the specific methods and results discussed are merely illustrative of the invention as described more fully in the claims that follow thereafter.

Experimental Details

Overview

The present application discloses a reliable assay for the preparation of highly fragmented and chemically modified FFPE-RNA, prior to IVT-amplification and high-throughput analyses. This strategy has been termed complementary-template reverse-transcription (CT-RT) because it allows for the restoration of short single-stranded cDNA primers reverse-transcribed from FFPE-RNA, by annealing and reverse-transcription of complementary sense-RNA-templates. A comparison was made between matched 10 year-old frozen and 10 year-old FFPE-RNA using this strategy and an already established T7 IVT-amplification method using cDNA microarrays (Van Gelder et al. 1990). The CT-RT process increases the specificity and the amount of available sequence, thus providing larger transcripts for subsequent IVT amplification. The CT-RT process is highly reproducible and yielded higher signal in cDNA microarray experiments than through direct T7 IVT-amplification of FFPE-RNA. Using the same RNA-template library, single stranded DNA (ssDNA) sequences obtained from either archived colon or breast tissues were restored and the retrieval of genes specific to each tissue was demonstrated. This strategy demonstrated that poly-A transcripts recovered from older archived tissues provide valuable information with regard to gene signatures.

Materials and Methods

Reagents. Universal human reference (UHR) RNA was purchased from Stratagene. Its quality was verified on a Bioanalyzer 2100 expert (Agilent). Linear amplifications were performed using the MessageAmp II aRNA amplification kit from Ambion. The sense RNA template library was generated with the SenseAmp RNA amplification kit from Genisphere (Goff et al. 2004).

RNA extraction from matched frozen and formalin-fixed tissues. Matched 10 year-old frozen and 10 year-old formalin-fixed and paraffin-embedded (FFPE) breast cancer samples were obtained from the Montefiore Medical center, Bronx, N.Y. RNA from 10-year-old frozen tissue was extracted using TriZol reagent following the manufacturer's instructions (Invitrogen). RNA from 4 year-old colon cancer, 8 year-old breast cancer and 10-year-old formalin-fixed and paraffin-embedded breast cancer tissue was macro-dissected.

The FFPE tissue was de-paraffinized using 500 μl of Hemo-De at room temperature on an agitator, three times (Krafft et al. 1997). The tissue was washed with 1 ml of 100% RNase-free ethanol three times and also three times with 1 ml of 95% RNase-free ethanol on ice, for 8 minutes each time (Stanta et al. 1998). The tissue was then washed with 1 ml of 1×PBS DEPC treated and incubated in 200 μl of RNase-Free 1×PBS and 6.5 μl of RNase-Out (Invitrogen) for 90 minutes on ice, for rehydration. Prior to proteinase K digestion, the tissue was homogenized in a 7 ml Wheaton homogenizer using 2.010 ml digesting buffer (50 mM Tris-HCl pH7.5, 75 mM NaCl, 5 mM $CaCl_2$ and 0.1% SDS). The homogenized tissue was separated in fifteen tubes of 134 μl, to which was added 1 μl of RNase out (Invitrogen). A volume of 15 μl of proteinase K at 30 mg/ml was added to each tube (Roche Diagnostics). The Digestion was carried-out at 59° C. for one hour, upon agitation every 5 minutes. After one hour, digests were gathered in two tubes and spun down at 12,000 rpm for 1 nm. The pellets were kept on ice, while the supernatants were subjected to butanol-extraction to achieve a final volume of 100 μl. This solution was used to resuspend the tissue pellets and obtain a final 150 μl. The solution was homogenized in 1 ml of TriZol (Invitrogen) following the manufacturer's instructions. The RNA present in the supernatant was precipitated with 1 μl of 0.1 mg/ml of linear acrylamide and 3 M sodium acetate and 600 μl of isopropanol. The tubes were incubated for 12 hours at −20° C. and then spun at 14,000 rpm for 30 minutes at 4° C. The precipitated RNA was washed with 200 μl of 70% RNase-Free ethanol, dried and resuspended in RNase-Free Water (Promega). The RNA was quantified on a Nanodrop NO-100 spectrophotometer and analyzed on Bioanalyzer using the Agilent-2100 software.

First strand cDNA synthesis and purification for the CT-RT process. The synthesis of single-stranded DNA primers from FFPE-RNA was achieved by using 5 μg of RNA in a 20 μl reaction. As provided elsewhere in the application, a modified procedure can be used when using less than 5 micrograms of starting RNA material. For the reverse-transcription of the FFPE-RNA, Arrayscript (Ambion) was used, which uses the same enzyme as the one provided in the MessageAmp II RNA kit (Ambion). Each reaction contained 5 μg of RNA, 2 μl of 10× arrayscript buffer, 1 μl of RNase inhibitor mix, 4 μl dNTP mix 2.5 mM each (Ambion), 1 μl (10 ng) of T7-Oligo-$dT_{(24)}$-VN (5'-GGCCAGTGAATTGTAATACGACTCAC-TATAGGGAGGCGGdT$_{(24)}$-(A/C/G)(A/C/G/T)-3') (SEQ ID NO:23) and 1 μl of arrayscript reverse-transcriptase) at 42° C. for two hours (Ambion). The 20 μl reaction was brought to 400 μl with RNase-free water (Sigma) for purification on a microcon YM-50 (Millipore), following the manufacturer's instruction. The purification was performed by spinning the YM-50 at 500 g for 12 minutes to cut-off double stranded cDNA/RNA fragments under 100 bp and single-stranded T7-oligo$dT_{(24)}$-VN (SEQ ID NO:23). The filter was washed 3 times using 400 μl of RNase-free water (Sigma). A volume of 88 μl was recovered and incubated with 10 μl of 10× RNase H buffer and 2 μl of RNase H 10 U/μl (Ambion) for 30 min at 37° C. The solution was transferred to a boiling water-bath for 3 min and transferred on ice for 5 min. The single-stranded cDNA was purified using a MinElute purification column, following manufacturer's instruction (Qiagen). The single-stranded cDNA was recovered in 10 μl and measured on a Nanodrop NO-100 Spectrophotometer.

T7 in-vitro amplifications and CT-RT amplifications. The direct amplification of RNA extracted from 10 year-old frozen RNA and 10 year-old FFPE-RNA was performed with the MessageAmpII aRNA kit from Ambion, using five micrograms of total RNA for each reaction, as instructed by the manufacturer. The T7 IVT-amplifications proceeded for 14 hours at 37° C. For the restorations, the CT-RT process was performed using the single-stranded DNA primers obtained from five micrograms of FFPE-RNA. In order to prevent the T7-oligo $dT_{(24)}$ sequences of the purified cDNA primers from priming poly (A) sequences of random templates in the Sense-RNA template library, 1 μl of the Non-Sense Knock-out oligonucleotide (NSK), 5'-(A/C/T/G)(C/T/G)$dA_{(24)}$-CCGCCTCCCTATAGTGAGTCGTATTA-CAATTCACTGGCC-3' (SEQ ID NO:24) (0.5 μg/μl) was added to the 9 μl single-stranded cDNA. This solution was incubated at 70° C. for 10 min, 70-37° C. for 10 mins and at 37° C. for 10 minutes for hybridization. This solution was speed vacuum-dried to obtain a final volume of 1 μl. The universal human sense RNA template library was prepared using 2.5 μg of fresh universal human reference (UHR) RNA (Stratagene) and amplified using the SenseAmp RNA Amplification Kit from Genisphere, following the manufacturer's instructions. One minor change was made to the protocol by adding DNase-I, prior to sense-RNA purification. The UHR RNA integrity was checked on a Bioanalyzer (Agilent). The Sense-RNA was quantified using the Nanodrop, aliquoted in 10 μg/5 μl samples and kept at −80° C. For complementary-template reverse-transcription (CT-RT), 8.8. μl of SenseRNA was annealed with 1.2 μl of 10× first strand buffer and 1 μl of purified cDNA/NSK1 primers and one drop of RNase-free mineral oil (Sigma). The solution was incubated in a 0.5 μl microfuge PCR tube in a Perkin Elmer Cetus DNA Thermal Cycler with a thermocycle file (70° C. for 10 min, 70° C. to 42° C. in 90 min). The first strand cDNA synthesis was prepared by adding 1.2 μl of RNase-free water, 0.8 μl of 10× First Strand Buffer, 4 μl of dNTP mix, 1 μl of ribonuclease inhibitor and 1 μl of arrayscript reverse-transcriptase from the MessageAmp aRNA kit (Ambion) and added at the end of the cycle, at 42° C. and incubated for 2 hours at 42° C. At the end of the cycle the tube was transferred on ice. The second-strand cDNA synthesis mix was prepared (63 μl of RNase-free water, 10 μl of 10× second strand cDNA buffer, 4 μl of dNTPs, 2 μl of DNA polymerase and 1 μl of RNase-H) and added under the mineral oil to the 20 μl solution, following the manufacturer's instructions (Ambion). The tubes were incubated for 2 hours at 16° C., the cDNA was purified and the amplified RNA (aRNA) synthesized following the in-vitro transcription instructions for 14 hours (Ambion). The aRNA was quantified on a Nanodrop spectrophotometer and analyzed on a Bioanalyzer.

PCR analyses of double stranded DNA. Double-stranded cDNA material synthesized from 5 μg of UHR RNA, 10-years-old frozen RNA, 10-year-old FFPE RNA and 10 year-old FFPE cDNA after restoration was used in the PCR reactions. Half the volume of the cDNA recovered from each reaction was used to prepare a master-mix for each set of nine PCR reactions. Three sets of four primers (Invitrogen), containing three forward and one reverse-primer, were synthesized for the three corresponding genes, human Cyclin D1 (Ccnd1; GenBank Accession Number: 053056), human tumor protein 53 (p53; GenBank Accession Number: 000546) and human tyrosine-kinase type-receptor (HER-2/neu/ERBB2; GenBank Accession Number: 004448). For Ccnd1, from 5' to 3' end, forward primer 1; 5'-GT-GATGGGGCAAGGGCACAAGTC-3' (SEQ ID NO:1), primer 2; 5'-CGGCTGGGTCTGTGCATTTCTGG-3' (SEQ ID NO:2), primer 3; 5'-CCCAGCACCAACATGTAAC-CGGC-3' (SEQ ID NO:3) and reverse-primer 5'-TGGGGTTTTACCAGTTTTATTTC-3' (SEQ ID NO:4). For p53, from 5' to 3' end, forward-primer 1; 5'-GCTGGTCT-CAAACTCCTGGGCTC-3' (SEQ ID NO:5), primer 2;

5'-GTGGAGCTGGAAGGGTCAACATC-3' (SEQ ID NO:6), primer 3; 5'-CCCACCCTTCCCCTCCTTCTCCC-3' (SEQ ID NO:7) and reverse-primer; 5'-GCAGCAAAGTTT-TATTGTAAAATAAG-3' (SEQ ID NO:8). For Her-2, from 5' to 3' end, forward-primer 1; 5'-GCGACCCATTCA-GAGACTGTCCC-3' (SEQ ID NO:9), primer 2; 5'-GTGT-CAGTATCCAGGCTTTGTAC-3' (SEQ ID NO:10), primer 3; 5'-GGGGAGAATGGGTGTTGTATGGG-3' (SEQ ID NO:11) and reverse-primer; 5'-TGCAAATGGA-CAAAGTGGGTGTGGAG-3' (SEQ ID NO:12). Each forward-primer was paired with the corresponding reverse-primer for each gene (Ccnd1, p53 and Her-2). All PCR reactions were performed using the Platinum Taq DNA polymerase high-fidelity kit, in 50 µl reactions (Invitrogen). Each reaction contained 1 µl of cDNA, 2 µl of forward and reverse primer (1 µg/µl), 2 µl of 50 mM $MgCl_2$, 5 µl of 10× high fidelity buffer (600 mM Tris-$SO_4$ pH8.9, 180 mM ammonium sulfate), 5 µl of 0.2 mM of dNTP (2.5 mM), 33 µl of distilled water and a drop of mineral oil. Negative controls were performed using 1 µl of sterile distilled water instead of cDNA. Platinum Taq high-fidelity polymerase (2 µl of 0.5 unit/µl) was added after cDNA denaturation for 5 min at 95° C.; reactions were performed in a Perkin-Elmer Cetus DNA thermal-cycler for 30 cycles (95° C. for 1 min, 50° C. for 1 min 30 seconds and 68° C. for 2 minutes, ending with a final extension step at 68° C. for 10 min). The PCR amplicons were visualized using a UV light-box after electrophoresis on a 1.5% agarose gel containing 0.5 µg/µl ethidium bromide. The gels were photographed using a Fluorchem Imager (Alpha Innotech Corporation, CA).

Cy3/Cy5 labeling and microarray hybridization. The cRNA produced from each-amplification was used to produce fluorescent probes by reverse-transcription. For each microarray experiment, 5 µg of cRNA synthesized from UHR RNA (reference) and 5 µg of cRNA from the present samples were labeled. The aRNA was incubated in the presence of 2.67 µl of random primers (3 µg/µl) from Invitrogen in a final volume of 19 µl at 70° C. for 10 min, spun down and put on ice for 5 minutes. Labeling reactions were performed by adding 8 µl of 5× first-strand buffer, 4 µl of 0.1 M DTT, 4 µl of dNTP labeling mix (2.5 mM of each), 4 µl of 25 nM Cy3-labeled deoxyuridine triphosphate (Cy3-dUTP) for cRNA amplified from UHR (reference) or 4 µl of 25 nM Cy5-labeled deoxyuridine triphosphate (Cy5-dUTP; Amersham Pharmacia Biotech, NJ) for cRNA from the present samples, 1 µl of RNase-Out at 40 units/µl (Invitrogen), 1.5 µl of Superscript II reverse-transcriptase 200 units/µl (Invitrogen), and incubated at 42° C. for 1 hour. After one hour of incubation, 1.5 µl of Superscript II reverse-transcriptase was added for another 60 minutes at 42° C. The 40 µl reactions containing the labeled cDNAs were incubated in the presence of 44 µl of RNase-Free water, 10 µl of 10× RNase-One buffer and 2 µl of RNase-One 10 U/µl (Promega) for 35 min at 37° C. for removal of cRNA templates. The RNase-One was then inactivated by transferring the tubes at 95° C. for 3 min and kept on ice. The 100 µl of Cy3-labeled UHR cDNA and the 100 µl of Cy5-labeled sample cDNA were combined in a tube containing 200 µl sodium-acetate 3M (PH5.1), 2 µl of 0.1 µg/µl linear acrylamide (Ambion) and 500 µl of 100% ethanol, and precipitated at 14,000 RPM for 30 minutes. The probes were washed with 200 µl of 70% RNase-Free Ethanol and air-dried before being resuspended in 16.5 µl of RNase-Free water. The microarray slides were incubated at 50° C. with 60 µl of pre-hybridization buffer. The 16.5 µl probes were incubated with 40.5 µl of hybridization buffer and 3 µl of human block solution. The pre-hybridization and hybridization buffers were supplied by the AECOM microarray facility, and human block solution prepared as described by Belbin et al. (2002) (30). After an hour the slides were washed in distillated water and dried. The 60 µl labeled probe solution was added onto the slide and covered with a 22×22 Premium Cover Glass (Fisher) and placed in a sealed chamber in a water bath at 50° C. overnight, in the dark. The slides were washed the following day as described in Belbin et al. 2002. Dry slides were scanned using the GenePix 4000A microarray scanner (Axon Instruments, Foster City, Calif.). The UHR Cy3 (Green) and the FFPE-RNA Cy5 (Red) signal intensities were calculated using the GenePix Pro 6.0 Software.

cDNA Microarray experiments and statistical analyses. The microarray used for this study displayed a set of 28,032 sequence-verified human IMAGE (Integrated Molecular Analysis of Gene Expression) cDNA clones representing both known genes and expressed sequence tags. These cDNAs were designed and built at the Albert Einstein College of Medicine (AECOM), Bronx, N.Y. In all analyses, the mean background to the intensities was subtracted for the 2 channels. For each spot, the mean intensity of both channels was calculated and subtracted with the median of the background intensity.

Results

Method design. Given that the transcriptional profiling of degraded and chemically modified RNA harvested from FFPE tissue has been limited and has remained questionable, a strategy based on sequence restoration was developed as described herein and termed complementary-template reverse-transcription (CT-RT) (Masuda et al. 1999, Cronin et al. 2004). The RNA/cDNA duplex obtained by reverse-transcription of FFPE-RNA is filtered in order to exclude fragments shorter than 100 nucleotides and T7-oligo-$dT_{(24)}$ primers that have not be used (FIG. 1A). The cDNA is single-stranded by RNase-H removal of the RNA and then purified. A blocking primer, complementary to the T7-oligo-$dT_{(24)}$ sequence, is added to prevent annealing of the oligo-$dT_{(24)}$ to the poly (A) tail of sense-RNA templates. The sense-RNA template library is obtained by in-vitro transcription of a T7 promoter incorporated into the 3' end of the first strand cDNA, which provides RNA with the same orientation as messenger RNA (Goff et al. 2004) (FIG. 1B). Optimal annealing conditions between ssDNA and sense-RNA templates are obtained by using temperature gradient of 70° C. to 42° C. during a 90 minutes hybridization time (FIG. 1C). The reverse-transcription of the hybridized templates allows for the extension and thus restoration of ssDNA sequences. The process of CT-RT is followed by double-strand DNA synthesis, T7 IVT-amplification and cDNA microarray analysis of the cRNA.

Figure 2:
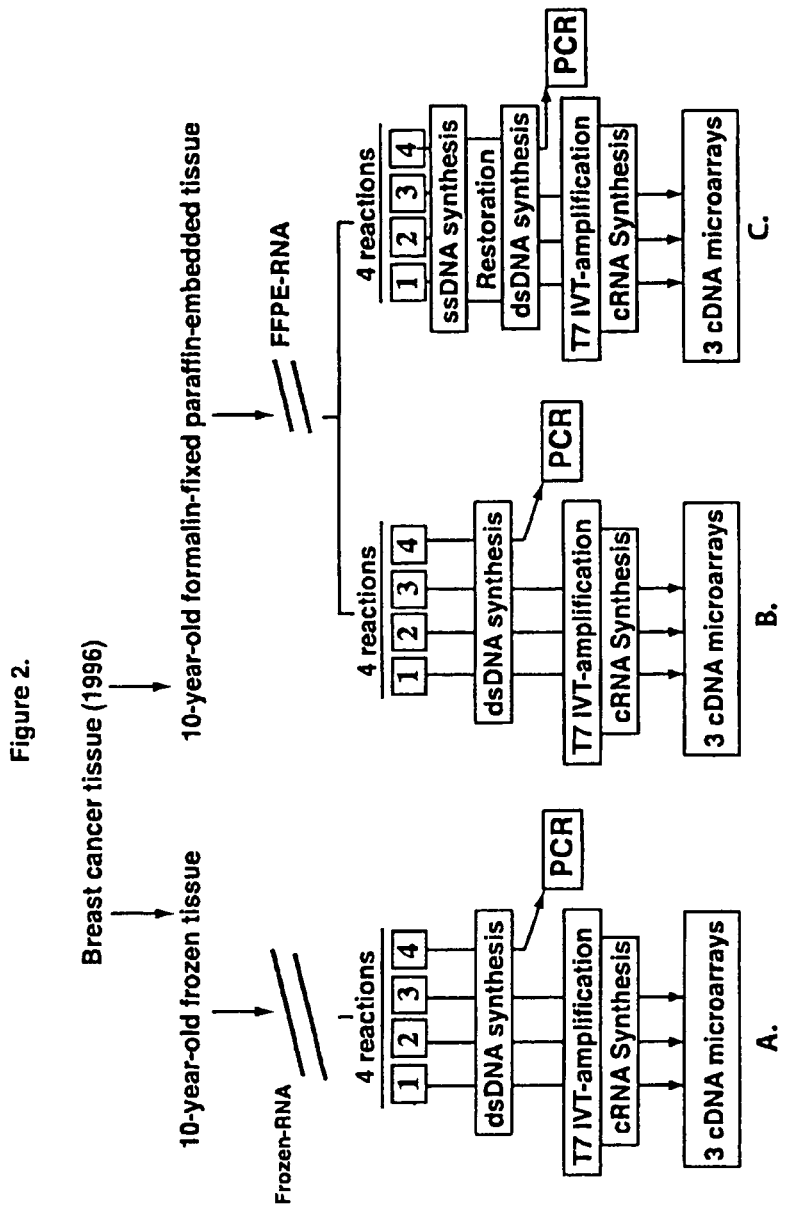
FIG. 2A-2C. Experimental procedure utilized for the analysis of a matched 10 year-old frozen and 10 year-old FFPE breast cancer sample. (A) Five micrograms of RNA extracted from the 10-year-old frozen portion of the sample is reverse-transcribed and the cDNA is double-stranded (ds-DNA) in four individual reactions. The dsDNA of three reactions undergoes IVT-amplification (MessageAmpII, Ambion), which gives rise to complementary-RNA (cRNA) for cDNA microarray analyses. The dsDNA of one reaction is used for PCR experiments. (B) Five micrograms of RNA extracted from the 10-year-old FFPE portion of the sample undergoes the exact same process. (C) Single-stranded DNA (ssDNA) obtained by reverse transcription of five micrograms of FFPE-RNA is purified and hybridized to the sense-RNA template library. The restored ssDNA is double stranded, and purified. Three of the CT-RT reactions undergo IVT-amplification, while the dsDNA of one reaction is used for PCR experiments.
Figure 3:
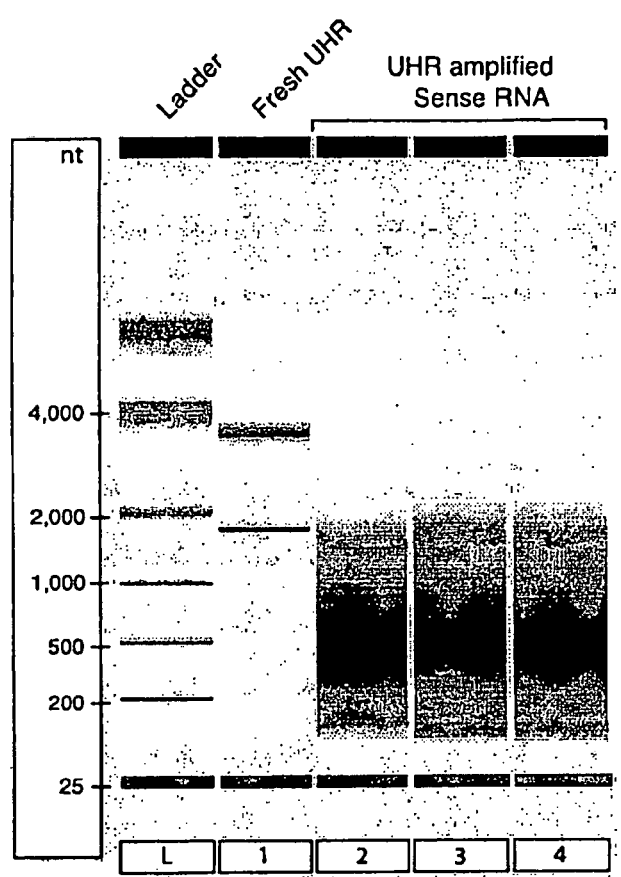
FIG. 3A-3C. Size distribution of mRNA, cRNA and dsDNA observed on Agilent 2100 Bioanalyzer 6000 Nanochips. (A) Observation of the UHR RNA and the sense-RNA template library integrity. Lane L displays the ladder (25, 200, 1,000, 2,000 and 4,000 nucleotides (nt)). Lane 1 contains total fresh universal human reference RNA. The ribosomal 18s, at 1,900 nt, and 28s, at 3,800 nt, RNA bands are characteristic of fresh RNA. Lanes 2, 3 and 4 display the size distribution of three individual IVT-amplifications of sense-RNA using total RNA displayed in lane 1. (B) Size distribution of fresh, frozen, FFPE-RNA and amplified cRNA. Lane L displays the ladder (25, 200, 1,000, 2,000 and 4,000 base pair). Lane 1 contains fresh human breast RNA, with 18s and 28s ribosomal RNA. Lane 2 contains total RNA extracted from a 10 year-old frozen human breast cancer tissue. Lane 3 contains total RNA extracted from the matched 10 year-old FFPE human breast cancer tissue. The 10 year-old frozen and FFPE-RNA were matched from the same patient and were obtained from the Montefiore Hospital, Bronx, N.Y. Lane 4, 5 and 6 contain amplified cRNA obtained from three individual IVT-amplifications of 10 year-old frozen RNA (lane 2). Lanes 7, 8 and 9 contain amplified cRNA obtained by direct IVT-amplification of the 10 year-old FFPE-RNA (lane 3) in three individual reactions. Lanes 10, 11 and 12 contain amplified cRNA obtained by CT-RT and IVT-amplification of the same 10 year-old FFPE-RNA, in three individual reactions. (C) Size distribution of double-stranded DNA on a Bioanalyzer 2100 Agilent nanochip. Lane L displays the ladder. Lane 1 displays the size distribution of dsDNA obtained from 10 year-old frozen RNA. Lane 2 displays the size distribution of dsDNA obtained by reverse-transcription and DNA double strand synthesis of 10 year-old FFPE-RNA. Lane 3 shows dsDNA obtained after CT-RT and double-strand DNA synthesis of the same 10 year-old FFPE-RNA.

CT-RT of a 10 year-old archived breast cancer sample. The present strategy was tested using matched 10 year-old frozen and 10 year-old FFPE breast cancer samples. After extracting RNA from the frozen tissue, one round of T7 IVT-amplification was applied to five micrograms of total RNA in four individual reactions (FIG. 2A). One of the reactions was stopped at the purification of double-stranded DNA for later PCR experiments, while the remaining three reactions underwent T7 IVT-amplification. RNA was extracted from the matching area of the FFPE breast cancer sample. A 260/280 ratio of 1.90 was obtained. To test the T7 IVT-amplification on FFPE-RNA, four reactions were prepared using 5 micrograms of FFPE-RNA in each (FIG. 2B). One of the reactions was only carried out to the synthesis of double stranded (dsDNA) and kept for PCR experiments, while the three remaining reactions underwent the entire process. Then, to evaluate the restoration strategy, four reactions were prepared using 5 micrograms of FFPE-RNA in each. Reverse-transcriptions were performed with the same reverse-tran scriptase as the one provided in the MessageAmpII amplification kit from Ambion (FIG. 2C). The ssDNAs were purified and hybridized for 90 minutes with 10 micrograms of sense-RNA template library. Prior to using the sense-RNA library, the quality of the amplified RNA obtained through three individual amplifications was checked on an Agilent bioanalyzer 2100 expert. The library contained templates with sizes distributing between 250 and 1,000 nucleotides, peaking at 500 nucleotides (FIG. 3A). After hybridization the CT-RT was performed by adding the reagents provided in the MessageAmpII aRNA kit (Ambion). The reactions were incubated for 2 hours at 42 degrees. The second-strand DNA synthesis was carried-out as instructed by the manufacturer (Ambion). One reaction was kept for PCR experiments, while the other three underwent T7 IVT-amplification for 14 hours.

Figure 3C:
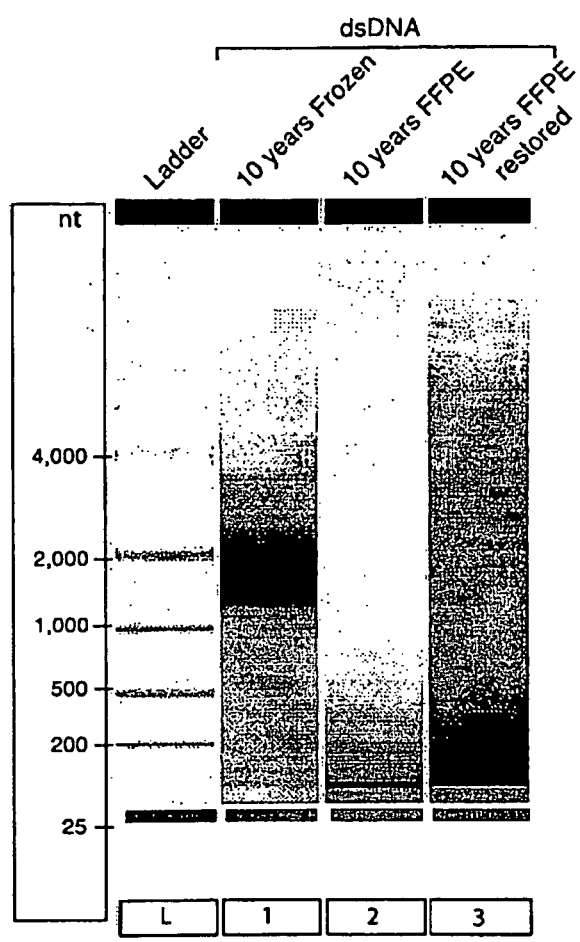
Figure 4A:
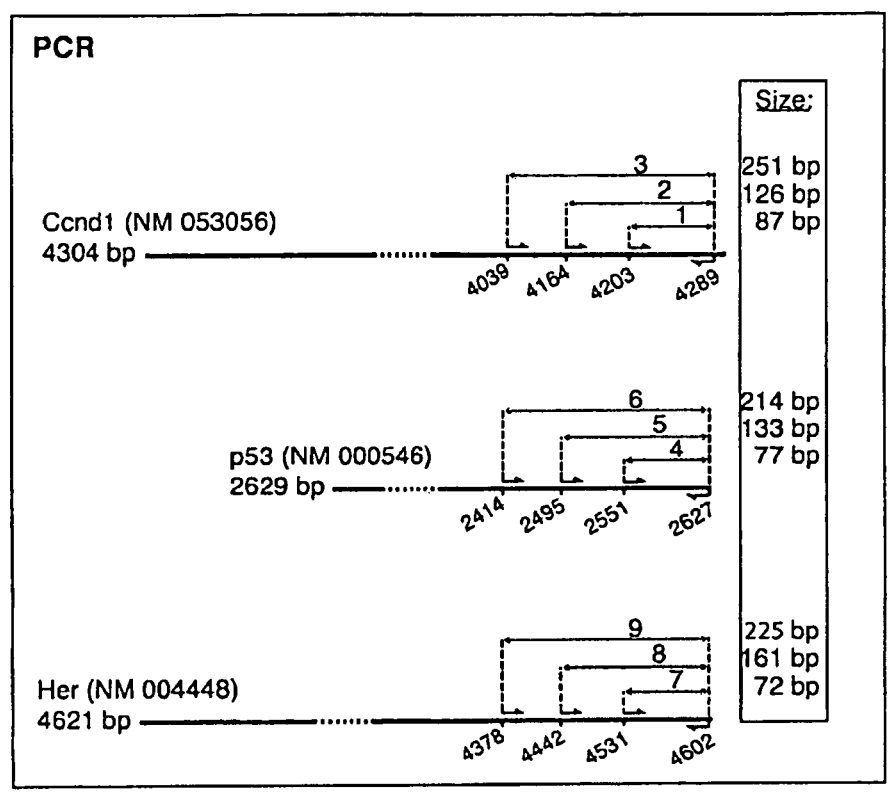

The CT-RT process provides larger cDNA and cRNA transcripts. In order to investigate the benefit of the CT-RT process over the reverse-transcription (RT) of short FFPE-RNAs, the size distribution of cRNA and cDNA products was compared for each of the reactions on a bioanalyzer 2100 Agilent. The 10 year-old frozen RNA displayed a degradation pattern with absence of 28s ribosomal RNA but still observable 18s RNA (FIG. 3B, lane 2). The T7 IVT-amplification of the frozen RNA gave rise to products ranging between 50 and 1,000 nucleotides, peaking at 200 nucleotides, in three individual reactions (lanes 4-6). These amplifications generated 105, 88 and 88.5 micrograms of cRNA. When the RNA extracted from the 10 year-old FFPE-RNA was analyzed, much smaller products with fragments smaller than 200 nucleotides were observed (lane 3). The T7 IVT-amplification of this FFPE-RNA gave rise to products ranging between 50 and 250 nucleotides, which peaked at 125 nucleotides, in each of the triplicates (lanes 7-9). Although the RNA was degraded, amplification reactions provided 44, 40.4 and 32.9 micrograms of cRNA, thereby sufficient amounts for microarray analyses. When the cRNA obtained by CT-RT performed on the same 10 year-old FFPE-RNA was analyzed, a large size increase was observed of the products that ranged between 50 and 850 nucleotides and peaked at 300 nucleotides (FIG. 3B, lanes 10-12). Interestingly, the CT-RT process produced lower amounts of cRNA, 28.2, 27.8 and 27.3 micrograms, suggesting that it may be more selective than reverse-transcription and direct IVT-amplification. Considering that the CT-RT process allowed for the increase of available DNA sequences, the dsDNA was observed on a Bioanalyzer 2100 Agilent (FIG. 3C). The dsDNA generated from 10 year-old frozen RNA appeared the largest with transcript sizes ranging between 1,000 and 2,000 nucleotides (lane 1). The dsDNA obtained by reverse-transcription of FFPE-RNA appeared the smallest with transcripts sizes no larger than 200 nucleotides (lane 2) whereas dsDNA restored by CT-RT of sense-RNA templates displayed products as large as 750 nucleotides (lane 3). Taken together these results indicate that frozen RNA provides a good template for IVT-amplification. Degraded FFPE-RNA, however, does not provide a good template for IVT-amplification as it produces very small cRNA molecules, but appears usable for CT-RT reactions and the production of larger transcripts.

cRNA transcripts obtained by CT-RT contain more gene-specific information. In order to verify that the increase of the cRNA size was due to the specific reverse-transcription of complementary templates, a PCR experiment was designed to test for the dsDNA transcript sizes. Three genes of significance for breast cancer were chosen, the human Cyclin D1 (Ccnd1), human tumor protein 53 (p53) and human tyrosine-kinase type-receptor (HER-2/neu/ERBB2) (Lebeau et al. 2003) (31). For each gene, three forward oligonucleotides increasingly spaced from the 3' end of the transcripts were designed. Then, by combining each of these forward primers with the same reverse primer in individual PCR reactions, the amount of sequence available from the 3' end of the dsDNA transcripts was determined for each of these genes (FIG. 4A). The PCR reactions were first tested in the absence of a known source of dsDNA, which did not generate any amplicons (FIG. 4B, panel 1). Using the dsDNA that was generated from UHR RNA, the presence of these three genes was determined and it was demonstrated that their RNA templates were larger than 250 nucleotides (panel 2). The same PCR reactions were then performed with dsDNA obtained from 10 year-old frozen RNA. Each of the three PCR products was detected for each gene (FIG. 4B, panel 3). Although the PCR experiments were performed with the same conditions as with UHR dsDNA, a higher number of non-specific products were detected. The presence of these non-specific products suggested that fragmented frozen RNA provided partial sequences allowing the annealing of the oligonucleotides. When PCR reactions were performed with dsDNA obtained from 10 year-old FFPE-RNA, the presence of these three genes was verified by observing the smallest amplicons (FIG. 4B, panel 4). The size of these products revealed that dsDNA templates did not exceed 150 bp, as fragments were not detected of 251 bp for Ccnd1, 214 bp for p53 and 225 bp for Her-2 (FIG. 4B, panel 4). These PCR results confirmed the bioanalyzer analyses, which suggested that 10 year-old FFPE-RNA mostly contained transcripts of 165 nucleotides. When the PCR reactions were performed with dsDNA that had been restored by CT-RT, each of the three products was detected for the three genes (FIG. 4B, panel 5). These PCR reactions verified that each of these genes was present but more importantly that the dsDNA of these three genes was larger after restoration. The specificity of the CT-RT process was verified by cloning and sequencing the largest amplicons (FIG. 4B, panel 5, lane 3, 6 and 9). Taken together these results demonstrated that the reverse-transcription of FFPE-RNA provides short but specific DNA transcripts that effectively match the ones detected in frozen RNA. When these cDNA transcripts were used for the CT-RT of complementary RNA-templates, a physical restoration of gene specific sequences was detected.

Figure 5:
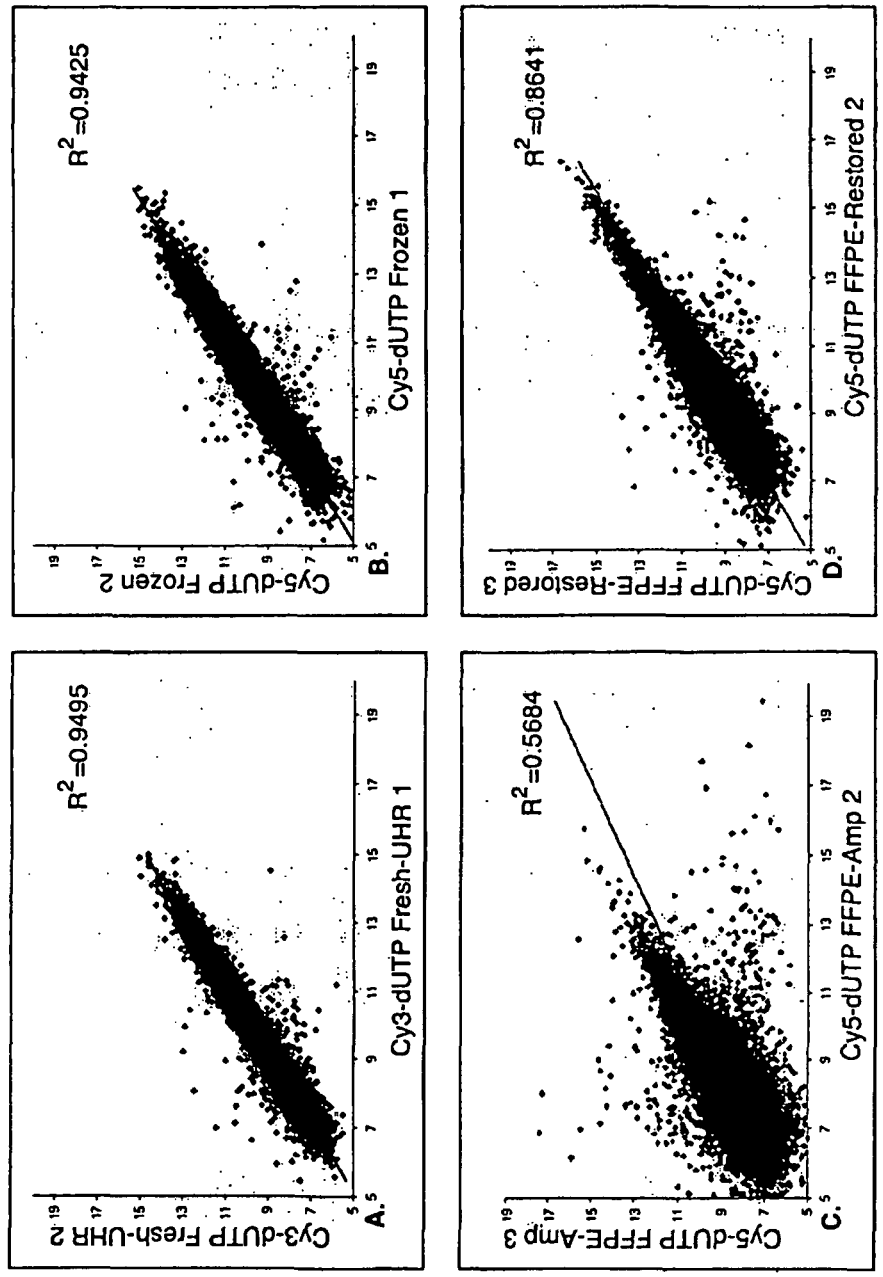
FIG. 5A-5D. Scatter plots comparing the $\log_2$ ratios of experimental repeats. The coefficient of determination $R^2$ represents the square of the correlation coefficient (r) and defines the strength of the linear relationship between repeats. (A) This panel displays the correlation between IVT-amplifications of fresh universal human reference RNA (FIG. 3A, lane 1) in the channel near 25 nt (Cy3), which was used as the reference for each cDNA microarray experiment. The coefficient of determination is displayed in the top right corner, $R^2=0.9495$. (B) This graph displays the correlation between IVT-amplifications 1 and 2 of 10 year-old frozen RNA (FIG. 3B, cRNA lane 4 and 5) in the channel for Cy5. The coefficient of determination between both experiments is displayed in the top right corner, $R^2=0.9425$. (C) The scatter plot shows the correlation between IVT-amplification 2 and 3 of 10 year-old FFPE-RNA (FIG. 3B, cRNA lane 8 and 9) in the channel for Cy5. The $R^2$ between FFPE-Amp2 and FFPE-Amp3 is displayed in the top right corner, and is 0.5684. (D) This scatter plot displays the correlation between CT-RT-IVT amplified restoration 2 and 3 using the same 10 year-old FFPE-RNA (FIG. 3B, lane 11 and 12) in the channel for Cy5. The coefficient of determination between restoration 2 and restoration 3 is displayed in the top right corner, $R^2=0.8641$.

The CT-RT process provides reliable cRNA for transcriptional profiling. In order to evaluate the robustness of the CT-RT of sense-RNA templates as a multiplex process, the cRNA obtained by IVT-amplification was analyzed on cDNA microarrays (FIG. 5). For quality control, each cDNA microarray was hybridized with both Cy5-labelled material (the experiment) and Cy3-labelled UHR cRNA (the reference). The reliability of IVT-amplification was investigated by analyzing the cRNA obtained from fresh UHR RNA (Cy3) on cDNA microarrays (FIG. 5A). The gene ratios between the technical repeats were compared. A high coefficient of determination ($R^2=0.9495$) was obtained, which demonstrated the strength of the linear relationship between repeats. Using cRNA amplified from partially degraded 10 year-old frozen RNA, a high coefficient of determination was also obtained (FIG. 5B, $R^2=0.9495$). These results demonstrated that the MessageAmpII aRNA kit from Ambion provided high performance IVT-amplifications even with partially degraded RNA. The quality of the cRNA amplified directly from 10 year-old FFPE-RNA was then evaluated. The coefficient of determination was much lower ($R^2$ between 0.5684 and 0.6201), thus demonstrating that the linear relationship between ratios obtained from technical repeats was impeded by the degradation and the chemically modification of FFPE-RNA (FIG. 5C). The robustness of the CT-RT process was then evaluated by analyzing the cRNA obtained after restoration and IVT-amplification of the same 10 year-old FFPE-RNA (FIG. 5D). The coefficient of determination was significantly higher ($R^2$ between 0.8621 and 0.8495), which demonstrated that ssDNAs, obtained from highly degraded and chemically modified material, provided a high quality material that could be reliably restored by CT-RT and amplified for cDNA microarray analysis.

Figure 6:
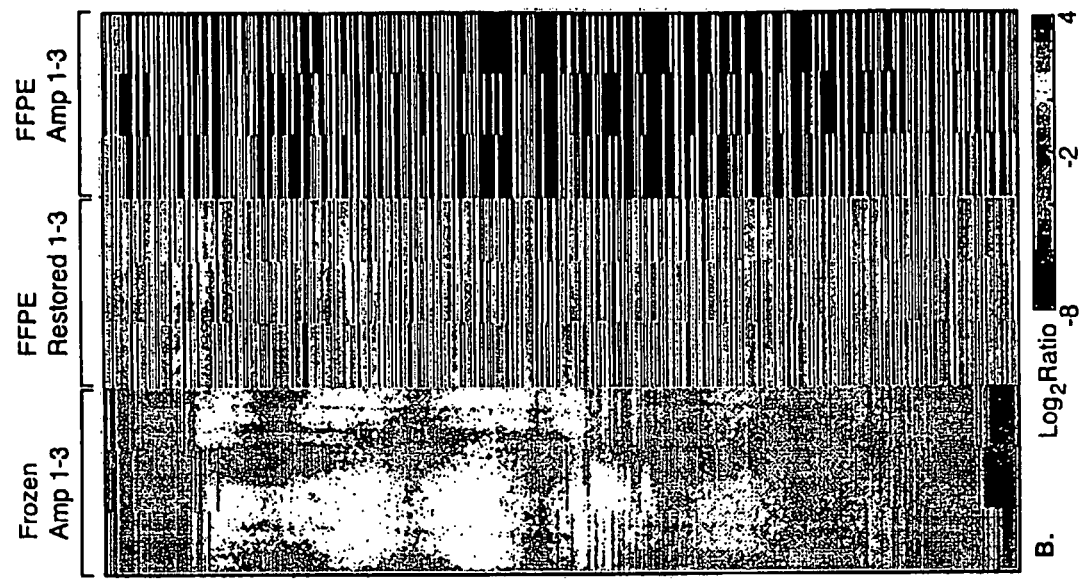
FIG. 6A-6B. Signal intensity and heat-map analysis of the correlation between the $\log_2$ ratios measured by cDNA microarrays. (A) Hybridization pictures of the same grid in the Cy5 channel across all microarrays. The top three panels display the three grids obtained with cRNA from 10 year-old frozen RNA (Frozen-Amp 1-3). The three mid-panels show the hybridization signal of cRNA obtained after restoration and IVT-amplification of 10 year-old FFPE-RNA in three individual experiments (FFPE-Restored 1-3). The three bottom-panels display the hybridization signal of cRNA obtained by direct IVT-amplification of 10 year-old FFPE-RNA in three individual experiments. (B) Heat-map displaying the $\log_2$ between −2 and 2 for the expression ratios of 1,044 genes detected in frozen tissue on a 28,032 features cDNA microarray. The ratios displayed were obtained after IVT-amplification of 10 year-old frozen RNA (Frozen-Amp 1-3), restoration and IVT-amplification of 10 year-old FFPE-RNA (FFPE-Restored 1-3) and direct IVT-amplification of 10 year-old FFPE-RNA (FFPE-Amp 1-3) from left to right. The expression ratios obtained after IVT-amplification of restoration and IVT-amplification of 10 year-old FFPE-RNA are measured between −8 and 4. Each column represents an individual hybridization and each line a different feature. The signal was generated by hybridization of the cRNA to the cDNA microarrays features. Shading near 4 represents upregulated genes and shading near −8 represents downregulated genes, respectively.
Figure 6:
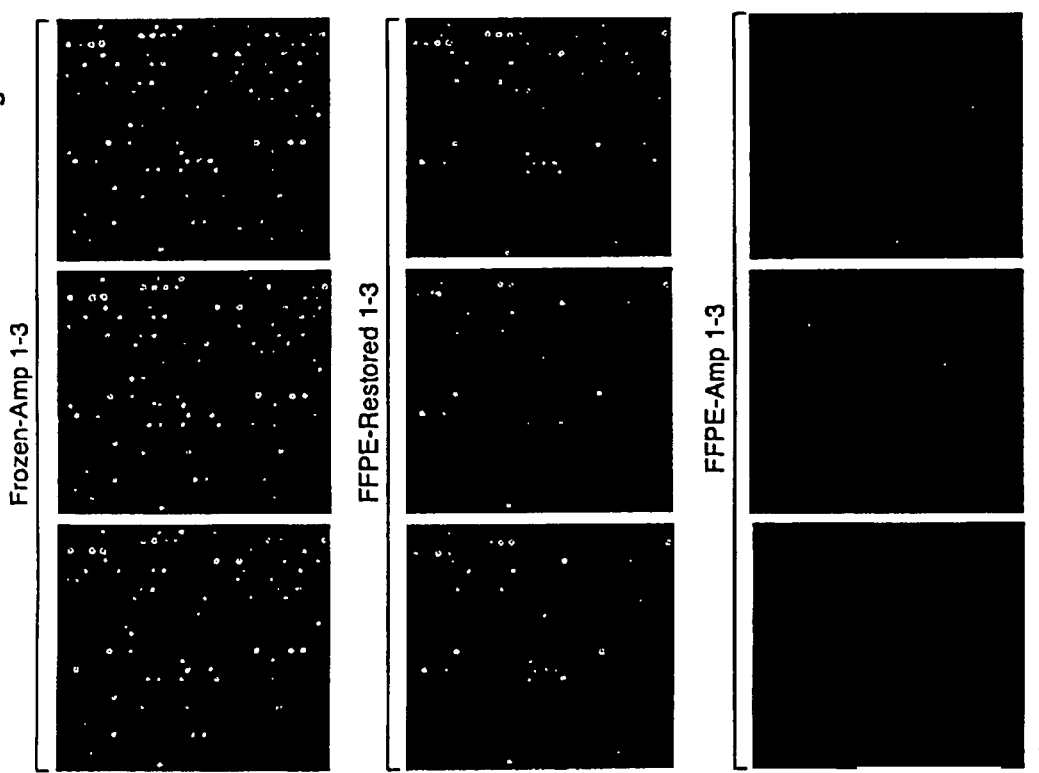

CT-RT improves the correlation between FFPE and frozen RNA expression profiles. The amount of information that could be recovered from the 10 year-old FFPE-RNA was evaluated by comparison with the 10 year-old frozen RNA, using either the CT-RT process or direct IVT-amplification. Using the microarray data, it was determined that the number of observable spots, with a signal higher than 1,000 in each the red (Cy5) and the green (Cy3) channels, was almost four times higher with the CT-RT process (4583) than by direct IVT-amplification of FFPE-RNA (1306; see Table 1). The data also revealed that the number of spots, with less than 20% of variability with the frozen material, was five times higher with the CT-RT process (2475) than by direct IVT-amplification (490) of the 10 year-old FFPE-RNA (Table 1). These results indicated that the CT-RT process allowed for a more reliable and a significantly higher recovery of features from the 10 year-old FFPE-RNA, which failed to be detected by direct IVT-amplification and microarray analysis. One sample grid was chosen from the different microarrays to exhibit the signal intensity generated by Cy5-labeled cRNA obtained from 10 year-old FFPE-RNA, by comparison with the 10 year-old frozen RNA (FIG. 6A, Frozen 1-3). It was observed that the signal intensities measured after restoration of the 10 year-old FFPE-RNA (FFPE-Restored 1-3) were lower than the ones measured with frozen RNA, but were almost undetectable by IVT-amplification of the 10 year-old FFPE-RNA (FFPE-Amp 1-3). Considering that the signal generated by FFPE-RNA was lower than frozen RNA, genes were analyzed with expression ratios ranging between 0.5 and 2. A selection was made of a set of genes detected in frozen RNA and in UHR RNA, utilized for the synthesis of sense-RNA templates, and a heat map was generated for 1,044 genes with expression ratios between 0.5 and 2 (FIG. 6B, Frozen-Amp 1-3). It was observed that the restoration of 10 year-old FFPE RNA (FFPE-Restored 1-3) provided a much larger set of genes with expression ratios overlapping the ones from frozen material than after direct IVT-amplification (FFPE-Amp 1-3). It was determined that the total number of genes recovered from 10 year-old FFPE-RNA with ratios matching the ones from frozen RNA was three times higher after restoration (3562) than after direct IVT-amplification (1218, see Table 2). Although the number of features was higher after restoration, the coefficient of determination remained four times higher ($R^2$=0.38) than after IVT-amplification of FFPE-RNA ($R^2$=0.10). When features were selected with expression ratios ranging between 0.5 and 2, more than three times the amount of genes were detected after restoration (2395) than after IVT-amplification (785). For these genes, the CT-RT process provided a coefficient of determination twenty five times higher ($R^2$=0.50) than the one obtained by IVT-amplification ($R^2$=0.02). Together, these results demonstrated that the restoration of FFPE-RNA provides access to a larger set of features, which display higher intensities possibly due to the elongation of the transcripts, and that correlate better with the ones detected in frozen RNA by comparison with direct IVT-amplification of FFPE-RNA.

CT-RT of different archived tissues provides tissue-specific transcripts. The reproducibility of the CT-RT process was assessed using two different types of archived tissues, and their expression-profiles were investigated for the presence of tissue-specific transcripts. For these experiments, total RNA was isolated from an eight year-old FFPE breast cancer tissue and from a four year-old FFPE colon cancer tissue. For each tissue, two CT-RT reactions were performed using the same amount of starting material with the same sense-RNA template library. The cRNA obtained by IVT-amplification of the restorations was analyzed on 8,000 features cDNA microarrays. Very high coefficients of determination were obtained for duplicate restorations of the four year-old colon cancer (FIG. 7A, $R^2$=0.94) and duplicate restorations of the eight year-old breast cancer FFPE-RNA (FIG. 7B, $R^2$=0.91). These results demonstrated that the CT-RT process can be applied reliably to material isolated from different types of FFPE tissues. As the restorations of these samples had been performed with the same sense-RNA template library, the transcriptional profiles of these two tissues were investigated for the presence of tissue-specific features. The analyses revealed the presence of genes specific to each of the colon and breast cancer tissues. Displays were made of 20 genes that were only detected in colon tissue, 20 genes specifically detected in the breast cancer tissue and 20 genes that were detected in each tissue (FIG. 7C). For the colon tissue, the mucosa was macro-dissected and the following genes identified: the peroxisome proliferator-activated receptor delta (PPARδ) that has been directly linked with colon cancer (Gupta et al. 2000) (32), the retinoblastoma 1 (RB1) gene (Pandey et al. 1995) (33), the phosphatidic acid phosphatase type 2 (PAP2) gene also detected in colon tissue (Sun et al. 2005) (34), the mucin gene (Song et al. 2005) (35) and the keratin 19 gene (Whitehead et al. 1999) (36). For the breast cancer tissue that had been macro-dissected, the following genes were identified: the collagen type VI gene (Iyengar et al. 2005) (37), the fibroblast growth factor 3 gene (Naidu et al. 2001) (38), the VE-cadherin gene (Parker et al. 2004) (39), the BCL2 gene (Neri et al. 2006) (40), the Nitric oxide synthase (Tse et al. 2005) (41), the collagen type IV and I genes (Ioachim et al 2002 (42), Cloos et al. 2003 (43)), the plexin A1 gene (Bachelder et al. 2003) (44), and the cytoskeleton regulatory protein hMena (ENAH) gene (Di Modugno et al. 2004) (45). Also identified were common genes for both of these tissues, which displayed differential expression levels, for example the TP53, the protein kinase D1, and the glyceraldhyde-3-phosphate dehydrogenase (GAPDH) genes. These experiments demonstrated that messenger RNA, recovered from FFPE tissue, can be utilized for the recovery of tissue-specific transcripts by reverse-transcription of complementary RNA templates represented in a sense-RNA template library. The CT-RT process is a molecular instrument that allows for identification of tissue-specific transcripts by microarray analyses

TABLE 1

Observable features after IVT-amplification of 10 year-old frozen, IVT-amplification of 10 year-old FFPE-RNA and restoration followed by IVT-amplification of 10 year-old FFPE-RNA.

| | Frozen | FFPE-Amplified | FFPE-Restored |
|---|---|---|---|
| Number of good spots | 25791 | 22838 | 22997 |
| Number of spots with red (Cy5) and green (Cy3) intensities ≧1,000 | 4535 | 1306 | 4583 |
| Number of measurements with variability ≦20% | 2878 | 490 | 2475 |

TABLE 2

Correlation of the expression ratios between IVT-amplified 10 year-old frozen and IVT-amplified 10 year-old FFPE-RNA or between IVT-amplified 10 year-old frozen and restored IVT-amplified 10 year-old FFPE-RNA.

|  | Frozen vs FFPE-Amplified | | Frozen vs FFPE-Restored | |
| --- | --- | --- | --- | --- |
|  | Number of genes | $R^2$(Cy5) | Number of genes | $R^2$(Cy5) |
| Correlation between spots with intensities $\geq$1,000 | 1218 | 0.10 | 3562 | 0.38 |
| Correlation between spots with ratios between 0.5 and 2 | 785 | 0.02 | 2395 | 0.50 |

Discussion

Successful analyses of RNA extracted from archived samples have been achieved in targeted studies. One such example is the resolution of the crystal structure of a major surface antigen of the extinct 1918 "Spanish" influenza virus, which killed over 20 million people worldwide, and that was determined after reassembly of the hemagglutinin gene from viral RNA fragments retrieved from 1918 formalin-fixed lung tissues (Reid et al 2001; Stevens et al. 2004). The potential to prevent the occurrence of diseases or advance knowledge in cancer research resides in the ability to decipher the transcriptional profiles of clinical samples. Although RNA from FFPE tissue is fragmented and chemical modified, RT-PCR experiments have successfully demonstrated the presence of valuable stretches of information spanning over a 100 nucleotides (Cronin et al. 2004, Bibikova et al. 2004; Abrahamsen et al. 2003; Antonov et al. 2005). Taking advantage of the presence of these sequences, a strategy was devised as disclosed herein that allows the molecular restoration of lost sequences by copy of sense-RNA templates, in order to enable the retrospective high-throughput analysis of archived samples from any era.

Moderately degraded RNA, submitted to multiple rounds of IVT-amplifications has been shown to provide reasonable profiles in microarray analyses (Schoor et al. 2004). Similar studies using IVT-amplifications based on the random priming of artificially degraded RNA indicated that microarray analyses might also be feasible with FFPE-RNA (Xiang et al. 2003; Tomlins et al. 2006). It has been shown, however, that the extent of fragmentation significantly increases with archive storage time, which suggests that the amount of RNA sequences available may decrease too detrimentally for the use of these techniques and the efficient detection of transcripts by microarray analysis (Cronin et al. 2004). The present results strongly corroborated these findings, as RNA recovered from the 10 year-old archived tissue appeared largely degraded, with fragments peaking at 165 nucleotides and overall smaller than 200 nucleotides. When 10 year-old FFPE-RNA was amplified, using the well-established T7-oligo-dT IVT-amplification, microarray analyses revealed that the correlation between technical repeats ranged between 0.5 and 0.6. Although sufficient amounts of complementary RNA were obtained for microarray analyses, the overall short size of the products may have contributed to the generation of non-specific signal. In the analysis of FFPE-RNA, the process of IVT-amplification may have primarily benefited to short transcripts, non-specific messages or other species of RNA and contributed to the increased non-specific signal.

In order to improve the quality of the signal measured in microarray experiments, the complementary-template reverse-transcription (CT-RT) of single-stranded DNA molecules generated from the 10 year-old FFPE-RNA was tested. The bioanalyzer results demonstrated that both cDNA and cRNA synthesized by IVT-amplification from CT-RT material produced larger molecules. Similarly, PCR experiments targeting the 3' end of the cDNA molecules obtained by CT-RT demonstrated an increase in sequence of at least 100 nucleotides for each gene tested. By cloning and sequencing the largest PCR products it was verified that the increase in the sequences was gene specific. These experiments demonstrated that short ssDNA molecules, representing the 3' end of these genes, carried sequences providing specificity for annealing to complementary templates. Although the process of CT-RT added steps of purification and extension for the preparation of cDNAs, it appeared to be highly reproducible. The correlation obtained between technical repeats ranged between 0.84 and 0.86, for material as old as 10 years and 0.9 for material ranging between 4 and 8 years. Therefore, the MessageAmpII IVT-amplification kit from Ambion demonstrated to be very efficient with FFPE-RNA as well as with the 10 year-old frozen RNA, which IVT-amplification resulted in ratios ranging between 0.94 and 0.96. When looking at the amount of genes detectable in FFPE-RNA, with intensity superior to 1,000, 4 times more genes were detected after CT-RT than by direct IVT-amplification. When looking at genes with expression ratios ranging between 0.5 and 2, the CT-RT allowed the retrieval of 50% of the genes by comparison with the matched frozen tissue. Unfortunately, the direct IVT-amplification of the FFPE-RNA only provided 2% of those genes by comparison with the frozen tissue. Taken together, the present results demonstrated that the addition of the CT-RT process, when using FFPE-RNA, significantly improved the performance of the IVT-amplification and the quality of the microarray experiments.

The CT-RT process takes advantage of a pluripotent sense-RNA template library that provides access to thousands of transcripts that have undergone IVT-amplification and thus are available in excess. Furthermore, when using the same sense-RNA template library for hybridization of 3' biased single-stranded DNA sequences reverse-transcribed from either colon or breast FFPE-RNA, tissue specific transcripts were identified and distinct transcriptional profiles were obtained. These results demonstrated that the 3' anchor region recovered from fragmented RNA contained the specificity required for gene identification. The analysis of 3' untranslated regions has been shown to provide valuable information with regard to transcript and isoform identity (Edwards-Gilbert, 1997; Hughes, 2006). Additionally, the present experiments demonstrated that CT-RT is a multiplex process that can be performed simultaneously in more than 3,000 transcripts in a single reaction.

Altogether these results demonstrated that RNA extracted from older archived material, although degraded and chemically modified, contains valuable 3' biased sequences. These sequences, which failed to be identified after direct IVT-amplification and microarray analysis, could be recovered after complementary-template reverse-transcription (CT-RT) and IVT-amplification. The restoration of single-stranded DNA transcripts, obtained from older FFPE-RNA, may become a valuable tool for the retrieval and linkage of genes to clinical parameters. The CT-RT process may be improved by increasing the recovery of cDNA primers, obtained by reverse-transcription of fragmented FFPE-RNA. The purification of FFPE-RNA may substantially be facilitated by using T7-oligo $dT_{(24)}$ primers bound to micro-beads, which may provide better mRNA recovery and thus improve the process of restoration by increasing the amount of available cDNA transcripts (55). Restored transcripts bound to the micro-beads may provide stable cDNA libraries, which may be reusable for multiple IVT-amplifications. Furthermore, this purification technique may facilitate the amenability of the restoration process to smaller FFPE-RNA samples.

Gene expression profiling of formalin-fixed and paraffin-embedded (FFPE) specimens, banked from completed clinical trials and routine clinical care, has the potential to yield valuable information implicating and linking genes with clinical parameters. However, microarray analyses of highly fragmented and chemically modified RNA has not provided reproducible measurements. Thus, in order to synthesize high-quality cDNA for T7 or T3 in-vitro transcription (IVT) amplification, a strategy was designed based on the restoration of short single-stranded cDNA sequences. This approach can be described as complementary-template reverse-transcription (CT-RT) because the short single-stranded oligo-$dT_{24}$-VN-ssDNA sequences reverse-transcribed from FFPE-RNA are used for the reverse-transcription of complementary sense-RNA templates, represented in a universal sense-RNA template library. The T7 IVT-amplification of CT-RT transcripts, obtained from FFPE-RNA, displays higher correlation ratios between technical repeats and yields to the detection of transcriptional profiles not detectable by direct T7 IVT-amplification. The demonstration that CT-RT can distinguish between gene signatures of breast and colon FFPE samples is an example that the present process is a meaningful and robust tool for the transcriptional profiling of older archived tissues.

REFERENCES

1. Mohr, S., Leikauf, G. D., Keith, G. and Rihn, B. H. Microarrays as cancer keys: an array of possibilities. (2002) *J Clin Oncol*, 20, 3165-75.
2. Perou, C. M., Sorlie, T., Eisen, M. B., van de Rijn, M., Jeffrey, S. S., Rees, C. A., Pollack, J. R., Ross, D. T., Johnsen, H., Akslen, L. A. et al. (2000) Molecular portraits of human breast tumours. *Nature*, 406, 747-52.
3. Sorlie, T., Perou, C. M., Tibshirani, R., Aas, T., Geisler, S., Johnsen, H., Hastie, T., Eisen, M. B., van de Rijn, M., Jeffrey, S. S. et al. (2001) Gene expression patterns of breast carcinomas distinguish tumor subclasses with clinical implications. *Proc Natl Acad Sci USA.*, 98, 10869-74.
4. Sorlie, T., Tibshirani, R., Parker, J., Hastie, T., Marron, J. S., Nobel, A., Deng, S., Johnsen, H., Pesich, R., Geisler, S. et al. (2003) Repeated observation of breast tumor subtypes in independent gene expression data sets. *Proc Natl Acad Sci USA.*, 100, 8418-23.
5. Golub, T. R. (2001) Genome-wide views of cancer. *N. Engl. J. Med.*, 344, 601-2.
6. Abramovitz, M. and Leyland-Jones, B. R. (2006) A Systems Approach to Clinical Oncology: Focus on Breast Cancer. *Proteome Sci.* 4, 5.
7. Dietel, M. and Sers, C. (2006) Personalized medicine and development of targeted therapies: the upcoming challenge for diagnostic molecular pathology. A review. *Virchows Arch.*, 448, 744-55.
8. Werner, M., Chott, A., Fabiano, A. and Battifora, H. (2000) Effect of formalin tissue fixation and processing on immunohistochemistry. *Am. J. Surg. Pathol.*, 24, 1016-9.
9. Krafft, A. E., Duncan, B. W., Bijwaard, K. E., Taubenberger, J. K. and Lichy, J. H. (1997) Optimization of the Isolation and Amplification of RNA From Formalin-fixed, Paraffin-embedded Tissue: The Armed Forces Institute of Pathology Experience and Literature Review. *Mol Diagn.*, 2, 217-230.
10. Stanta, G., Bonin, S. and Perin, R. (1998) RNA extraction from formalin-fixed and paraffin-embedded tissues. *Methods Mol Biol.*, 86, 23-6.
11. Masuda, N., Ohnishi, T., Kawamoto, S., Monden, M. and Okubo, K. (1999) Analysis of chemical modification of RNA from formalin-fixed samples and optimization of molecular biology applications for such samples. *Nucleic Acids Res.*, 27, 4436-43.
12. Coombs, N. J., Gough, A. C. and Primrose, J. N. (1999) Optimisation of DNA and RNA extraction from archival formalin-fixed tissue. *Nucleic Acids Res.*, 27, e12.
13. Cronin, M., Pho, M., Dutta, D., Stephans, J. C., Shak, S., Kiefer, M. C., Esteban, J. M. and Baker, J. B. (2004) Measurement of gene expression in archival paraffin-embedded tissues: development and performance of a 92-gene reverse transcriptase-polymerase chain reaction assay. *Am J Pathol.*, 164, 35-42.
14. Lehmann, U. and Kreipe, H. (2001) Real-time PCR analysis of DNA and RNA extracted from formalin-fixed and paraffin-embedded biopsies. *Methods*, 25, 409-18.
15. Lewis, F., Maughan, N. J., Smith, V., Hillan, K. and Quirke, P. (2001) Unlocking the archive—gene expression in paraffin-embedded tissue. *J. Pathol.*, 195, 66-71.
16. Relf, B. L., Machaalani, R. and Waters, K. A. (2002) Retrieval of mRNA from paraffin-embedded human infant brain tissue for non-radioactive in situ hybridization using oligonucleotides. *J. Neurosci Methods*, 115, 129-36.
17. Capodieci, P., Donovan, M., Buchinsky, H., Jeffers, Y., Cordon-Cardo, C., Gerald, W., Edelson, J., Shenoy, S. M. and Singer, R. H. (2005) Gene expression profiling in single cells within tissue. *Nat. Methods*, 2, 663-5.
18. Paik, S., Kim, C. Y., Song, Y. K. and Kim, W. S. (2005) Technology insight: Application of molecular techniques to formalin-fixed paraffin-embedded tissues from breast cancer. *Nat Clin Pract Oncol.*, 2, 246-54.
19. Bibikova, M., Talantov, D., Chudin, E., Yeakley, J. M., Chen, J., Doucet, D., Wickham, E., Atkins, D., Barker, D., Chee, M. et al. (2004) Quantitative gene expression profiling in formalin-fixed, paraffin-embedded tissues using universal bead arrays. *Am. J pathol.*, 165, 1799-807.
20. Bibikova, M., Yeakley, J. M., Chudin, E., Chen, J., Wickham, E., Wang-Rodriguez, J., and Fan, J. B. (2004) Gene expression profiles in formalin-fixed, paraffin-embedded tissues obtained with a novel assay for microarray analysis. *Clin. Chem.*, 50, 2384-6.
21. Ma, X. J., Patel, R., Wang, X., Salunga, J., Desai, R., Tuggle, J. T., Wang, W., Chu, S., Stecker, K., Raja, R. et al. (2006) Molecular classification of human cancers using a 92 real-time quantitative polymerase chain reaction assay. *Arch Pathol. Lab. Med.*, 130, 465-73.

22. Karsten, S. L., Van Deerlin, V. M., Sabatti, C., Gill, L. H. and Geschwind, D. H. (2002) An evaluation of tyramide signal amplification and archived fixed and frozen tissue in microarray gene expression analysis. *Nucleic Acids Res.*, 30, e4.

23. Klur, S., Toy, K., Williams, M. P. and Certa, U. (2004) Evaluation of procedures for amplification of small-size samples for hybridization on microarrays. *Genomics*, 83, 508-517.

24. Xiang, C. C., Chen, M., Ma, L., Phan, Q. N., Inman, J. M., Kozhich, O. A. and Brownstein, M. J. (2003) A new strategy to amplify degraded RNA from small tissue samples for microarray studies. *Nucleic Acids Res.*, 31, e53.

25. Wang, J, Hu, L., Hamilton, S. R., Coombes, K. R. and Zhang W. (2003) RNA amplification strategies for cDNA microarray experiments. *Biotechniques*, 34, 394400.

26. Onken, M. D., Worley, L. A., Ehlers, J. P. and Harbour, J. W. (2004) Gene expression profiling in uveal melanoma reveals two molecular classes and predicts metastatic death. *Cancer Res.*, 64, 7205-7209

27. Chung, C. H., Parker, J. S., Ely, K., Carter, J., Yi, Y., Murphy, B. A., Ang, K. K., El-Naggar, A. K., Zanation, A. M., Cmelak, A. J. et al. (2006) Gene expression profiles identify epithelial-to-mesenchymal transition and activation of nuclear factor-(kappa)B signaling as characteristics of a high-risk head and neck squamous cell carcinoma. *Cancer Res.*, 66, 8210-18.

28. Van Gelder, R. N., von Zastrow, M. E., Yool, A., Dement, W. C., Barchas, J. D. and Eberwine, J. H. (1990) Amplified RNA synthesized from limited quantities of heterogeneous cDNA. *Proc. Natl. Acad. Sci. USA.*, 87, 1663-7.

29. Goff, L. A., Bowers, J., Schwalm, J., Howerton, K., Getts, R. C. and Hart, R. P. (2004) Evaluation of sense-strand mRNA amplification by comparative quantitative PCR. *BMC Genomics*, 5, 76.

30. Belbin, T. J., Bhuvanesh, S., Barber, I., Socci, N., Wenig, B., Smith, R., Prystowsky, M. B., and Childs, G. (2002) Molecular classification of head and neck squamous cell carcinoma using cDNA microarrays. *Cancer Res.*, 62, 1184-90.

31. Lebeau, A., Unholzer, A., Amann, G., Kronawitter, M., Bauerfeind, I., Sendelhofert, A., Iff, A. and Lohrs, U. (2003) EGFR, HER-2/neu, cyclin D1, p21 and p53 in correlation to cell proliferation and steroid hormone receptor status in ductal carcinoma in-situ of the breast. *Breast Cancer Res. Treat.*, 79, 187-98.

32. Gupta, R. A., Tan, J., Krause, W. F., Geraci, M. W., Willson, T. M., Dey, S. K. and DuBois, R. N. (2000) Prostacyclin-mediated activation of peroxisome proliferator-activated receptor delta in colorectal cancer. *Proc. Natl. Acad Sci. USA*, 97, 13275-80.

33. Pandey, S., Gordon, P. H. and Wang, E. (1995) Expression of proliferation-specific genes in the mucosa adjacent to colon carcinoma. *Dis. Colon Rectum.*, 38, 462-7.

34. Sun, L., Gu, S., Sun, Y., Zheng, D., Wu, Q., Li, X., Dai, J., Dai, J., Ji, C., Xie, Y. and Mao, Y. (2005) Cloning and characterization of a novel human phosphatidic acid phosphatase type 2, PAP2d, with two different transcripts PAP2d_v1 and PAP2d_v2. *Mol. Cell. Biochem.*, 272, 91-6.

35. Song, S., Byrd, J. C., Koo, J. S. and Bresalier, R. S. (2005) Bile acids induce MUC2 overexpression in human colon carcinoma cells. Cancer, 103, 1606-14.

36. Whitehead, R. H., Demmler, K., Rockman, S. P. and Watson, N. K. (1999) Clonogenic growth of epithelial cells from normal colonic mucosa from both mice and humans. *Gastroenterology*, 117, 858-65.

37. Iyengar, P., Espina, V., Williams, T. W., Lin, Y., Berry, D., Jelicks, L. A., Lee, H., Temple, K., Graves, R., Pollard, J. et al. (2005) Adipocyte-derived collagen VI affects early mammary tumor progression in vivo, demonstrating a critical interaction in the tumor/stroma microenvironment. *J. Clin. Invest.*, 115, 1163-76.

38. Naidu, R., Wahab, N. A., Yadav, M., Kutty, M. K. and Nair, S. (2001) Detection of amplified int-2/FGF-3 gene in primary breast carcinomas using differential polymerase chain reaction. *Int. J. Mol. Med.*, 8, 193-8.

39. Parker, B. S., Argani, P., Cook, B. P., Liangfeng, H., Chartrand, S. D., Zhang, M., Saha, S., Bardelli, A., Jiang, Y., St Martin, T. B. et al. (2004) Alterations in vascular gene expression in invasive breast carcinoma. *Cancer Res.*, 64, 7857-66.

40. Neri, A., Marrelli, D., Roviello, F., DeMarco, G., Mariani, F., DeStefano, A., Megha, T., Caruso, S., Corso, G., Cioppa, T. and Pinto, E. (2006) Bcl-2 expression correlates with lymphovascular invasion and long-term prognosis in breast cancer. *Breast Cancer Res. Treat.*, 99, 77-83.

41. Tse, G. M., Wong, F. C., Tsang, A. K., Lee, C. S., Lui, P. C., Lo, A. W., Law, B. K., Scolyer, R. A., Karim, R. Z. and Putti, T. C. (2005) Stromal nitric oxide synthase (NOS) expression correlates with the grade of mammary phyllodes tumour. *J. Clin. Pathol.*, 58, 600-4.

42. Ioachim, E., Charchanti, A., Briasoulis, E., Karavasilis, V., Tsanou, H., Arvanitis, D. L., Agnantis, N. J. and Pavlidis, N. (2002) Immunohistochemical expression of extracellular matrix components tenascin, fibronectin, collagen type IV and laminin in breast cancer: their prognostic value and role in tumour invasion and progression. *Eur. J. Cancer.*, 38, 2362-70.

43. Cloos, P. A., Christgau, S., Lyubimova, N., Body, J. J., Qvist, P. and Christiansen, C. (2003) Breast cancer patients with bone metastases are characterised by increased levels of nonisomerised type I collagen fragments. *Breast Cancer Res.*, 5, R103-9.

44. Bachelder, R. E., Lipscomb, E. A., Lin, X., Wendt, M. A., Chadborn, N. H., Eickholt, B. J. and Mercurio, A. M. (2003) Competing autocrine pathways involving alternative neuropilin-1 ligands regulate chemotaxis of carcinoma cells. *Cancer Res.*, 63, 5230-3.

45. Di Modugno F, Bronzi G, Scanlan M J, Del Bello D, Cascioli S, Venturo I, Botti C, Nicotra M R, Mottolese M, Natali P G. et al. (2004) Human Mena protein, a serex-defined antigen overexpressed in breast cancer eliciting both humoral and CD8+ T-cell immune response. *Int. J. Cancer.*, 109, 909-18.

46. Reid, A. H., Taubenberger, J. K. and Fanning, T. G. (2001) The 1918 spanish influenza: integrating history and Biology. *Microbes Infect.*, 3, 81.

47. Stevens, J., Corper, A. L., Basler, C. F., Taubenberger, J. K., Palese, P. and Wilson, I. A. (2004) Structure of the uncleaved human H1 hemagglutinin from the extinct 1918 influenza virus. *Science*, 303, 1866-70.

48. Abrahamsen, H. N., Steiniche, T., Nexo, E., Hamilton-Dutoi, S. J., and Sorensen, B. S. (2003) Towards quantitative mRNA analysis in paraffin-embedded tissues using real-time reverse transcriptase-polymerase chain reaction: a methodological study on lymph nodes from melanoma patients. *J. Mol. Dagn.*, 5, 34-41.

49. Antonov, J., Goldstein, D. R., Oberli, A., Baltzer, A., Pirotta, M., Fleischmann, A., Alternatt, H. J., and Jaggi, R. (2005) Reliable Expression measurements from degraded RNA by quantitative real-time PCR depend on short amplicons and a proper normalization. *Lab. Invest.*, 85, 1040-50.
50. Schoor, O., Weinschenk, T., Hennenlotter, J., Corvin, S., Stenzl, A., Rammensee, H-G. and Stefanovic, S. (2003) Moderate degradation does not preclude microarray analysis of small amounts of RNA. *Biotechniques*, 35, 1192-201.
51. Tomlins, S. A., Mehra, R., Rhodes, D. R., Shah, R. B., Rubin, M. A., Bruening, E., Makarov, V. and Chinnaiyan, A. M. (2006) Whole transcriptome amplification for gene expression profiling and development of molecular archives. *Neoplasia*, 8, 153-62.
52. Edwalds-Gilbert, G., Veraldi, K. L., and Milcarek, C. (1997) Alternative poly(A) site selection in complex transcription units: means to an end. *Nucleic Acids Res.*, 25, 2547-61.
53. Hughes, T. A. (2006) Regulation of gene expression by alternative untranslated regions. *Trends Genet.*, 22, 119-22.
54. De Andres, B., del Pozo, V., Gallardo, S., de Arruda-Chaves, E., Cardaba, B., Martin-Orozco, E., Posada, M., Palomino, P. and Lahoz, C. (1995) Improved method for mRNA extraction from paraffin-embedded tissues. *Biotechniques*, 18, 42-44.

What is claimed is:

1. A method of restoring nucleic acid sequences recovered fragmented or degraded from a tissue comprising:

a) reverse transcribing mRNA from the tissue using random primers or a 5'-promoter-oligo-dT(10-30)-VN-3' primer, or a combination of both, to obtain a RNA/DNA duplex made of mRNA and single-stranded cDNA that is complementary to the mRNA, wherein V is nucleotide A, C, or G; N is nucleotide A, C, G or T; and oligo-dT (10-30) is 10 to 30 deoxyribothymidines;

b) removing RNA from the RNA/DNA duplex of step a) to yield a single-stranded cDNA primer that is complementary to the mRNA;

c) purifying the single-stranded cDNA primer obtained in step b) to obtain a purified primer;

d) hybridizing the purified single-stranded cDNA primer from step c) to a single stranded oligonucleotide to obtain a partially double-stranded oligonucleotide complex with a single-stranded cDNA portion specific to a gene expressed in the tissue, wherein if the primer in step a) is a 5'-promoter-oligo-dT (10-30)-VN-3' primer, then the single stranded oligonucleotide in step d) is 5'-NB-oligo-dA(10-30)-complementary promoter-3', wherein B is nucleotide C, G or T; oligo-dA(10-30) is 10 to 30 deoxyriboadenosines; the number of oligo-dAs is the same as the number of oligo-dTs in the reverse-transcribing primer in step a); and the complementary promoter is complementary to the promoter in step a); and wherein if the primers in step a) are random primers, then the single stranded oligonucleotides in step d) comprise a complementary promoter that is complementary to the promoter in step a), a dideoxynucleotide at their 3' end, and the same numbers of nucleotides as the random primers in step a);

e) annealing the single-stranded cDNA portion of the partially double-stranded oligonucleotide complex formed in step d) with sense RNA to form a hybrid product comprising single-stranded sense RNA and cDNA primer that is complementary-bound to the single-stranded sense RNA;

f) reverse-transcribing the single-stranded sense RNA of the hybrid product obtained in step e) to extend and restore nucleic acid sequences on the cDNA primer that is complementary-bound to the single-stranded sense RNA to obtain a cDNA/sense RNA duplex; and g) synthesizing double-stranded DNA from the cDNA/sense RNA duplex obtained in step f) so as to obtain a double-stranded DNA that contains a restored nucleic acid sequence from the tissue.

2. The method of claim 1, wherein the primer in step a) comprises a primer pool having sequences that represent genes transcribed in the tissue, wherein the purified primer in step c) comprises a purified primer pool representative of messenger RNAs that have been transcribed by the tissue, wherein the sense RNA in step e) comprises a sense RNA library, and wherein the double-stranded DNA in step g) comprises restored nucleic acid sequences from the genes transcribed in the tissue.

3. The method of claim 1, wherein the double-stranded DNA in step g) comprises a promoter for in vitro transcription of the double-stranded DNA or polymerase chain reaction amplification.

4. The method of claim 3, which further comprises in vitro transcription of the double-stranded DNA from step g) to obtain RNA that is complementary (cRNA) to the mRNA of step a).

5. The method of claim 1, wherein the sense RNA, DNA or double-stranded DNA in step e) is attached to a surface.

6. The method of claim 5, wherein restoration of the nucleic acid sequence comprises insertion of labeling molecules, which can be quantified directly on the surface by an antibody or fluorescence.

7. A method of restoring and identifying nucleic acid sequences recovered fragmented or degraded from a tissue comprising:
a) reverse transcribing mRNA from the tissue using random primers or a 5'-promoter-oligo-dT(10-30)-VN-3 primer, or a combination of both, to obtain a RNA/DNA duplex made of mRNA and single-stranded cDNA that is complementary to the mRNA, wherein V is nucleotide A, C, or G; N is nucleotide A, C, G or T; and oligo-dT (10-30) is 10 to 30 deoxyribothymidines;
b) removing RNA from the RNA/DNA duplex of step a) to yield a single-stranded cDNA primer that is complementary to the mRNA;
c) purifying the single-stranded cDNA primer obtained in step b) to obtain a purified primer;
d) hybridizing the purified single-stranded cDNA primer from step c) to a single stranded oligonucleotide to obtain a partially double-stranded oligonucleotide complex with a single-stranded cDNA portion specific to a gene expressed in the tissue, wherein if the primer in step a) is a 5'-promoter-oligo-dT (10-30)-VN-3' primer, then the single stranded oligonucleotide in step d) is 5'-NB-oligo-dA(10-30)-complementary promoter-3', wherein B is nucleotide C, G or T; oligo-dA(10-30) is 10 to 30 deoxyriboadenosines; the number of oligo-dAs is the same as the number of oligo-dTs in the reverse-transcribing primer in step a); and the complementary promoter is complementary to the promoter in step a); and wherein if the primers in step a) are random primers, then the single stranded oligonucleotides in step d) comprise a complementary promoter that is complementary to the promoter in step a), a dideoxynucleotide at their 3' end, and the same numbers of nucleotides as the random primers in step a);

e) annealing the single-stranded cDNA portion of the partially double-stranded oligonucleotide complex formed in step d) to sense nucleic acid templates attached to a surface to form a hybrid product comprising single-stranded sense RNA and cDNA primer that is complementary-bound to the single-stranded sense RNA; and f) incorporating a dye into the hybrid product attached to the surface using DNA or RNA polymerase to form a labeled hybrid product, so as to identify genes that are restored by copy of the template bound to the surface.

8. The method of claim 1, which further comprises after step a) and before step b), purifying the RNA/DNA duplex.

9. The method of claim 8, wherein purification excludes nucleic acid fragments shorter than 75 nucleotides and excludes primers that have not been used for reverse-transcription of fragmented polyA messenger RNA.

10. The method of claim 8, wherein purification eliminates single-stranded primer and short double strands of DNA and RNA, wherein the RNA comprises a poly A tail and less than 10 nucleotides of genetic information.

11. The method of claim 1, wherein the primer in step a) is a 5'-promoter-oligo-dT(10-30)-VN-3' primer, a 5'-T7-oligo-dT(10-30)-VN-3' (SEQ ID NO:17) primer or a 5'-T3-oligo-dT(10-30)-VN-3' (SEQ ID NO:18) primer.

12. The method of claim 1, wherein the random primers in step a) comprise 5'-promoter-oligo-N(10-30)-3 primers and the single stranded oligonucleotides in step d) comprise 5'-complementary promoter-oligo-N(10-30)-ddN-3', wherein oligo-N(10-30) is 10 to 30 N, wherein N is nucleotide A, C, T or G, and wherein ddN is a dideoxynucleotide.

13. A method of restoring nucleic acid sequences recovered fragmented or degraded from a tissue comprising:
a) obtaining a pool of single stranded cDNA primers that have been synthesized from either degraded or formalin-fixed RNA by reverse-transcription of the RNA;
b) creating a double-stranded region on the primer pool with blocking primer 5'-NB-oligo dA (10-30)-complementary-promoter-3' in order to provide a single stranded region for annealing with sense-RNA templates, wherein N is nucleotide A, C, G or T; B is nucleotide C, G or T; oligo-dA(10-30) is 10 to 30 deoxyriboadenosines; and the complementary promoter is complementary to the promoter in the primers in step a);
c) annealing the single-stranded cDNA primers with sense RNA to form a hybrid product comprising single-stranded sense RNA and cDNA primer that is complementary-bound to the single-stranded sense RNA;

d) reverse-transcribing the single-stranded sense RNA of the hybrid product obtained in step c) to extend and restore nucleic acid sequences on the cDNA primer that is complementary-bound to the single-stranded sense RNA to obtain a cDNA/sense RNA duplex; and
e) synthesizing double-stranded DNA from the cDNA/sense RNA duplex obtained in step d) so as to obtain a double-stranded DNA that contains a restored nucleic acid sequence from the tissue.

14. A method of restoring nucleic acid sequences directly onto a solid surface using amplified material obtained from degraded or formalin-fixed and paraffin-embedded RNA, where the method comprises:
   a) amplifying mRNA containing a poly dA tail from a sample of RNA in order to obtain cRNA;
   b) reverse-transcribing the cRNA with random primers into single-stranded cDNA primers, where the cDNA has the same orientation as mRNA and carries a poly dA tail;
   c) binding the cDNA primers to a 5'-biotin-promoter-oligo-dT(10-30)-VN-3' primer attached to microbeads, wherein V is nucleotide A, C, or G; N is nucleotide A, C, G or T; and oligo-dT(10-30) is 10 to 30 deoxyribothymidines;
   d) synthesizing a DNA strand complementary to the single-stranded cDNA primers directly onto the beads;
   e) purifying the microbeads from the single-stranded cDNA primers;
   f) creating a double-stranded region on the elongated primers carried by the microbeads with blocking primer 5'-NB-oligo dA (10-30)-complementary-promoter-3 in order to provide a single stranded region for annealing with sense-RNA templates, wherein N is nucleotide A, C, G or T; B is nucleotide C, G or T; oligo-dA(10-30) is 10 to 30 deoxyriboadenosines; and the complementary promoter is complementary to the promoter in the primers in step c);
   g) annealing the single-stranded cDNA primers with sense RNA to form a hybrid product comprising single-stranded sense RNA and cDNA primer that is complementary-bound to the single-stranded sense RNA;
   h) reverse-transcribing the single-stranded sense RNA of the hybrid product obtained in step g) to extend and restore nucleic acid sequences on the cDNA primer, bound to the microbead, that is complementary-bound to the single-stranded sense RNA to obtain a cDNA/sense RNA duplex; and
   i) synthesizing double-stranded DNA from the cDNA/sense RNA duplex obtained in step h) so as to obtain a double-stranded DNA that contains a restored nucleic acid sequence from the tissue.

15. A method of restoring nucleic acid sequences when starting with less than five micrograms of degraded or formalin-fixed and paraffin-embedded total RNA, the method comprising:
   a) reverse transcribing mRNA from the tissue using T7 or T3 random primers or a 5'-promoter-oligo-dT(10-30)-VN-3' primer, or a combination of both, to obtain a RNA/DNA duplex made of mRNA and single-stranded cDNA that is complementary to the mRNA, wherein V is nucleotide A, C, or G; N is nucleotide A, C, G or T; and oligo-dT(10-30) is 10 to 30 deoxyribothymidines;
   b) synthesizing double-stranded cDNA duplex using DNA polymerase I in the presence of RNase-H and purifying the double-stranded products on a column;
   c) increasing the amount of single-stranded DNA sequences, complementary to the messenger RNA, by combining the double-stranded cDNA duplex with 100 nanograms to one micrograms of 5'-promoter-oligo-dT (10-30)-VN-3' primer in the presence of a DNA polymerase for 5-40 cycles of polymerization;
   d) polymerizing the single-stranded DNA sequences by subjecting the mix obtained in c) to 5 to 40 cycles of 95 degree Celsius for 1 minute, 95 to 50 degree Celsius for 1 minute, 50 degree Celsius for 2 minutes and 72 degree Celsius for 2 minutes;
   e) purifying the single-stranded DNA from step d);
   f) hybridizing the purified single-stranded cDNA primer from step e) to a single stranded oligonucleotide to obtain a partially double-stranded oligonucleotide complex with a single-stranded cDNA portion specific to a gene expressed in the tissue,
   wherein if the printer in step a) is a 5'-promoter-oligo-dT (10-30)-VN-3' primer, then the single stranded oligonucleotide in step f) is 5'-NB-oligo-dA(10-30)-complementary promoter-3', wherein B is nucleotide C, G or T; oligo-dA(10-30) is 10 to 30 deoxyriboadenosines; the number of oligo-dAs is the same as the number of oligo-dTs in the reverse-transcribing primer in step a); and the complementary promoter is complementary to the promoter in step a); and
   wherein if the primers in step a) are T7 or T3 random primers, then the single stranded oligonucleotides in step f) comprise a complementary promoter that is complementary to the promoter in step a), a dideoxy-nucleotide at their 3' end, and the same numbers of nucleotides as the random primers in step a);
   g) annealing the single-stranded cDNA portion of the partially double-stranded oligonucleotide complex formed in step f) to sense nucleic acid templates to form a hybrid product comprising single-stranded sense RNA and cDNA primer that is complementary-bound to the sense nucleic acid;
   h) reverse-transcribing the single-stranded sense RNA of the hybrid product obtained in step g) to extend and restore nucleic acid sequences onto the cDNA primer that is complementary-bound to the single-stranded sense RNA to obtain a cDNA/sense RNA duplex; and
   i) synthesizing double-stranded DNA from the cDNA/sense RNA duplex obtained in step g) so as to obtain a double-stranded DNA that contains a restored nucleic acid sequence from the tissue.

16. The method of claim 1, wherein use of 5'-NB-oligo-dA (10-30)-complementary promoter-3' to obtain a partially double-stranded oligonucleotide complex prevents non-specific binding of oligo-dT(10-30) to the polyA tail of random sense-RNA templates represented in a sense-RNA template library.

17. A method of identifying the expression of disease-related genes in a subject comprising restoring a nucleic acid sequence from a tissue sample from the subject using the method of claim 1.

18. The method of claim 1, wherein the RNA/DNA duplex is purified before removing RNA from the duplex so as to exclude fragments shorter than 75 nucleotides and unused primers.

* * * * *